United States Patent

Akkerman et al.

[11] 4,012,392
[45] Mar. 15, 1977

[54] 2-BENZYL-4-PIPERIDONES USEFUL AS INTERMEDIATES IN THE PRODUCTION OF 6,7-BENZOMORPHAN DERIVATIVES

[75] Inventors: Antony Marie Akkerman, Amsterdam, Netherlands; Paul Adriaan Jan Janssen, Vosselaar, Belgium

[73] Assignee: ACF Chemiefarma N.V., Maarssen, Netherlands

[22] Filed: Jan. 23, 1975

[21] Appl. No.: 543,352

Related U.S. Application Data

[62] Division of Ser. No. 331,764, Feb. 12, 1973, Pat. No. 3,883,536, which is a division of Ser. No. 41,079, May 27, 1970, Pat. No. 3,764,606.

[30] Foreign Application Priority Data

June 4, 1969 Netherlands .................. 6908527
June 4, 1969 Netherlands .................. 6908528
June 4, 1969 Netherlands .................. 6908529

[52] U.S. Cl. .............. 260/293.8; 260/293.66; 260/293.83; 260/293.84; 424/267
[51] Int. Cl.² ............ C07D 211/44; C07D 221/20
[58] Field of Search ............... 260/293.66, 293.8

[56] References Cited

UNITED STATES PATENTS 3,883,536   5/1975   Akkerman et al. ........... 260/293.66

OTHER PUBLICATIONS

Teotino, J. Org. Chem. 27: 1906–1908 (1962).
Takeda et al., J. Org. Chem. 34: 4154–4160 (1969).

Primary Examiner—Henry R. Jiles
Assistant Examiner—Robert T. Bond
Attorney, Agent, or Firm—Alvin Sinderbrand

[57] ABSTRACT

6,7-benzomorphan derivatives having analgesic and morphine-antagonistic properties are of the formula

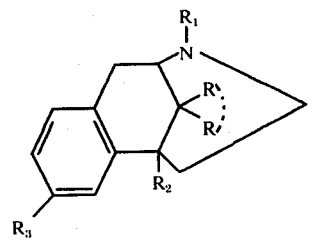

in which the substituents R are either lower alkyl groups or groups which, together with the carbon atom to which they are bonded, form a cycloaliphatic ring, and the substituents $R_1$, $R_2$ and $R_3$ may or may not be made and, if made, $R_1$ represents either a hydrogen atom or an alkyl, haloalkyl, alkenyl, alkinyl, aralkyl, cycloalkenyl, cycloalkylalkyl, cycloalkenylalkyl or cycloalkylidine-alkyl group, $R_2$ is an alkyl, aryl, heteroaryl or aralkyl group, and $R_3$ is a hydrogen atom or an hydroxy, alkoxy, alkoxy-alkoxy or acyloxy group. Such 6,7-benzomorphans may be in the form of their optically active enantiomers and/or their therapeutically acceptable salts. There are also disclosed methods for producing such 6,7-benzomorphan derivatives, and intermediates useful in such production.

3 Claims, No Drawings

2-BENZYL-4-PIPERIDONES USEFUL AS INTERMEDIATES IN THE PRODUCTION OF 6,7-BENZOMORPHAN DERIVATIVES

This is a division of application Ser. No. 331,764, filed Feb. 12, 1973, now U.S. Pat. No. 3,883,536 and which is a division of the prior application Ser. No. 41,079, filed May 27, 1970 and issued as U.S. Pat. No. 3,764,606 on Oct. 9, 1973.

The invention relates to new 6,7-benzomorphan derivatives, methods for the preparation of these compounds and new intermediates which are useful in obtaining such derivatives.

The synthesis of 6,7-benzomorphans was described for the first time by E. L. May and J. G. Murphy, J. Org. Chem. 20, 257 (1955). Since then, compounds of this type have drawn attention by reason of their interesting pharmacological properties. In particular, 6,7-benzomorphans not only show strong analgesic activity, but can also display activities which may be considered antagonistic to the action of morphine, depending on the nature of the substituent at the ring nitrogen atom. Such a combination of properties may lead to analgesic drugs practically devoid of the usual side effects of the classic strong analgesics, such as depression of respiration, development of tolerance and addiction.

Since the above publication of May et al. several series of 6,7-benzomorphans have been synthesized and identified, for example, as in U.S. Pat. Nos. 2,924,603, No. 3,033,867 and No. 3,138,603.

Moreover new drugs of this type have appeared, for instance, phenazocine and pentazocine, both of which have been introduced in therapeutics, and cyclazocine. Alternative routes of synthesis to arrive at 6,7-benzomorphans have been described, for example, in U.S. Pat. No. 3,073,837 and No. 3,093,650.

The chemistry and the pharmacology concerning 6,7-benzomorphans have been reviewed by N. B. Eddy and E. L. May in: International Series of Monographs in Organic Chemistry, Vol. 8, Part II (B), Pergamon Press (1966).

The existing literature indicates that, in order to possess high activity, 6,7-benzomorphan compounds must have a quaternary carbon atom at position 5 in the ring system, whereas, at position 9, the carbon atom should be preferably tertiary, at least, if the nomenclature "quaternary carbon atom" is restricted to those connected exclusively to other carbon atoms not belonging to functional groups. Heretofore, no publications have appeared concerning 6,7-benzomorphans having a quaternary carbon atom at position 9. The methods commonly used in the synthesis of benzomorphans are not feasible for the preparation of this type of compounds.

Now it has been found that 6,7-benzomorphans with the general formula

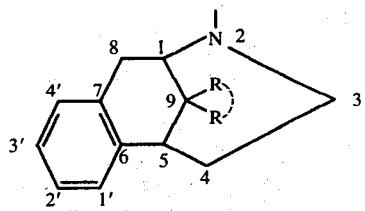

Formula I that is, with two substituents at position 9, and wherein both substituents R represent two small alkyl groups or, in combination with the carbon atom at position 9, represent a cycloaliphatic ring, and moreover wherein additional substituents may be present at positions 2,2' and 5, display interesting analgesic and/or morphine-antagonistic activities and/or may serve as intermediates in the preparation of compounds with such properties.

Of particular importance are the derivatives with the formula

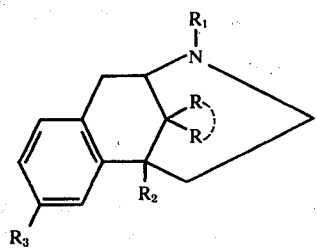

Formula II in which both constituents R have the above defined meaning, $R_1$ is a hydrogen atom or an alkyl, haloalkyl, alkenyl, alkinyl, aralkyl, cycloalkylalkyl, cycloalkenyl, cycloalkenylalkyl or cycloalkylidenealkyl group, preferably containing no more than nine carbon atoms, $R_2$ is an alkyl, aryl, heteroaryl or aralkyl group and $R_3$ is a hydrogen atom or a hydroxy, alkoxy, alkoxyalkoxy or acyloxy group. Particularly preferred are those derivatives in which $R_1$ is a hydrogen atom or a methyl, allyl, 3-methyl-2-butenyl, cyclopropylmethyl, cyclobutylmethyl or phenethyl group.

The new compounds according to the invention may be resolved into optical enantiomers, and pharamacological evaluation of the enantiomers has demonstrated that the desired activity resides largely in the levoratatory enantiomers.

The new compounds according to the invention may be administered as such or in the form of their therapeutically acceptable salts, in the usual manner.

As stated already, the compounds according to the invention cannot be prepared by processes commonly used in benzomorphan chemistry. Therefore, new routes for their synthesis have had to be devised.

In elaborating these new routes, it has been found possible to prepare the preferred compounds by means of cyclization of new substituted 2-benzyl-4-piperidinols of the general formula

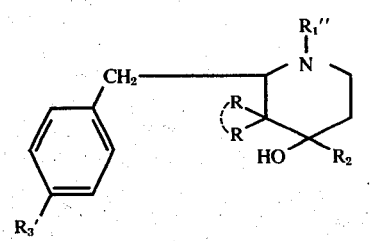

Formula III in which the substituents R and R₂ have the above defined meanings, R"₁ is an alkyl or aralkyl group, and R'₃ stands for a hydrogen atom or a hydroxy or alkoxy group. If desired, the cyclization may be followed by the introduction of new substituents and/or by replacement of substituents already present.

The mechanism of the cyclization probably proceeds via a carbonium ion having the structure of the formula

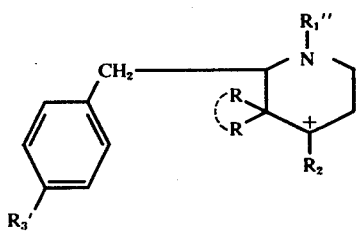

Formula IV

In principle, it should be possible to generate this carbonium ion in a different way, for instance from the corresponding 4,5-dehydropiperidine. In this case the above mentioned 4-piperidinol would be the obvious starting material. The cyclization of 2-benzyl-4-piperidinols has been described for the synthesis of already known benzomorphan derivatives by H. Henecka et al. In British patent specification 1,079,489. However, in said publication, the 4-piperidinols used do not have more than one substituent at position 3.

Another example of the cyclization of corresponding 4-piperidinols, however, devoid of any substituent at positions 3 and 4, has been published by M. Takeda et al. in J. Org. Chem. 34, 4154 (1969) after the priority date of the present application. The Dutch patent application 69.00081, also published after such priority date, discloses among other things, the preparation of N-acylbenzomorphans from N-acyl-2-benzyl-4-piperidinols, however, without any example and without an indication how these piperidinols should be prepared. For the sake of completeness mention may be made of Teotino (J. Org. Chem. 27 (1962,II), 1906) in which the author synthesized 1-methyl-2-benzyl-4-piperidinol as a potential precursor of 2-methyl-benzomorphan but did not describe the definitive cyclization.

The cyclization reaction described herein is preferably carried out at elevated temperatures and with the aid of a strong inorganic acid, preferably hydrobromic acid or phosphoric acid. During the reaction, alkoxy substituents at the benzene nucleus are converted into hydroxy groups.

Derivatives with R₁ = H are obtained from 2-methyl-benzomorphans according to Formula II, having R₁ = CH₃ by the known technique of von Braun, whereby these 2-methyl derivatives are treated with cyanogen bromide and the formed 2-cyano-benzomorphans are saponified and subsequently decarboxylated. Another route to benzomorphans unsubstituted at the nitrogen atom consists in removal of the benzyl group from the 2-benzyl analogues by catalytic hydrogenolysis.

Hereupon, other substituents may be introduced on the nitrogen atom according to methods which are usually applied in benzomorphan chemistry, such as reaction with alkylhalides or acylhalides. In the latter case amides are formed which can be reduced to tertiary amines by means of lithium aluminum hydride.

If both substituents at position 9 are the same or form part of a cycloalkane ring, the new benzomorphans, in contrast with the known derivatives with one substituent at that position, possess two instead of three asymmetric carbon atoms (namely C₁ and C₅).

Since the piperidine ring in the benzomorphan ring system can exist only in cis position relative to the remaining (tetralin-) part of the molecule, the new 6,7-benzomorphans can consequently arise only in one racemic form. To obtain optically active enantiomers of these new 6,7-benzomorphans, the resolution is carried out preferably with compounds having R₁ = H, whereupon the optically active substances obtained may be substituted on the nitrogen atom according to the methods described above. The resolution can be achieved advantageously with the aid of (−) and (+) 3-bromocamphor-8-sulphonic acid.

The previously mentioned intermediates according to Formula III, and also those wherein R₂ stands for an alkinyl group, have not been described hitherto in the literature. As stated above, related compounds having only one alkyl substituent at position 3 of the piperidine ring have been prepared by H. Henecka et al., for example, as described in British patent specification no. 1,078,286. However, they were prepared according to a method different from those described herein.

The new intermediates can be obtained by reduction of the corresponding 2-benzyl-4-piperidones having the formula

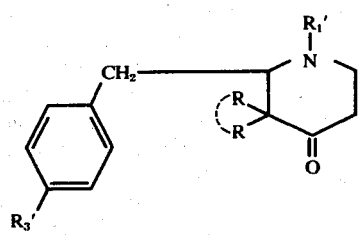

Formula V in which R'₁ is a hydrogen atom or an alkyl or aralkyl group, or by reaction with alkyl, alkinyl, aryl, aralkyl or heteroaryl metal compounds, preferably lithium compounds.

Said 4-piperidones were also not previously known and form part of the invention, which is also the case with the above-mentioned methods to convert them to the corresponding piperidinols.

For the preparation of the new piperidones according to Formula V two different new methods have been found. They will be described below as method 1 and method 2, respectively.

Method 1:

β-amino esters of the formula

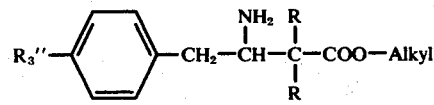

Formula VI in which R"₃ represents a hydrogen atom or an alkoxy group, are reacted with alkyl acrylates or with β-halopropionic esters, whereupon the products obtained may be substituted on the nitrogen atom. As a result, there are formed esters of 3,3—imino-dipropionic acid having the formula

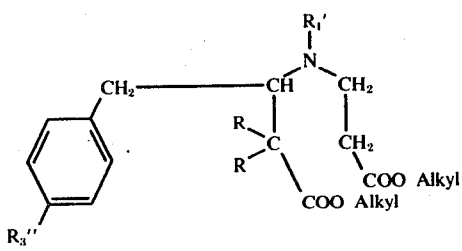

Formula VII in which $R'_1$ represents a hydrogen atom or an alkyl or aralkyl group. These imino esters are submitted to a Dieckmann cyclization process to provide alkyl 4-oxo-3-piperidine carboxylates having the formula

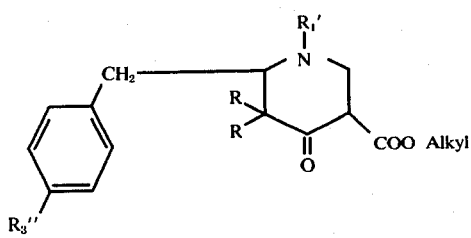

Formula VIII

Such alkyl 4-oxo-3-piperidine carboxylates are hydrolyzed and decarboxylated to give 4-piperidones having the formula

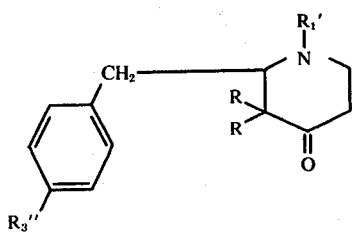

Formula IX

The amino esters of Formula VI, which are used as starting materials in this synthesis can be prepared from β-keto esters [Lapin et al., Gazz. Chim. Ital. 93, 451 (1963)] having the formula

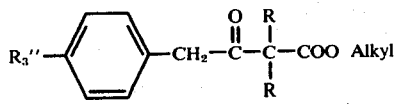

Formula X by conversion, with the aid of benzylamine, into benzylimino esters having the formula

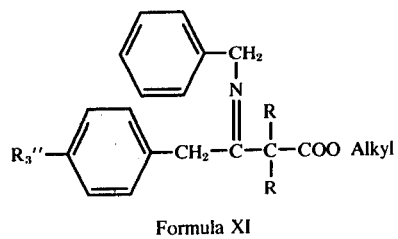

Formula XI

These benzylimino esters can be saturated by catalytic hydrogenation to afford benzylamino esters having the formula

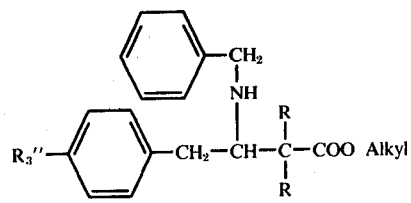

Formula XII

The N-benzyl group may be removed from the compounds of formula XII, by means of catalytic hydrogenolysis, to afford the desired amino esters of formula VI.

The conversion of the β-keto esters of formula X into the β-benzylimino esters of formula XI can be carried out in the usual way, that is, by reaction with benzylamine in the presence of a strongly acid catalyst (for instance p-toluenesulphonic acid or boron trifluoride diethyl etherate) in a solvent, such as toluene, which enables the removal of the formed water by means of azeotropic distillation. However, more profitably, the method of H. Weingarten et al., J. Org. Chem. 32, 3246 (1967), can be used, in which titanium tetrachloride acts as the condensing agent in an inert solvent, such as toluene, and at room temperature.

The reduction of the β-benzylimino esters to the β-benzylamino esters of the formula XII occurs by catalytic hydrogenation with platinum oxide as the catalyst. The removal of the benzyl group, giving rise to the above βamino esters of formula VI is effected by catalytic hydrogenolysis, with palladium as the preferred catalyst, for instance, palladium adsorbed at active charcoal. Said hydrogenation and hydrogenolysis are preferably carried out in an acid medium. Acetic acid, whether or not diluted with alcohol, appears to be a suitable solvent. These reductions can be carried out at atmospheric pressure and at room temperature.

The conversion of the β-amino esters of formula VI into the 3,3′-iminodipropionic esters of formula VII results from the reaction with β-halopropionic esters or, preferably, from the reaction with alkyl acrylates at an elevated temperature in the presence of acetic acid as a catalyst. The resulting imino esters can be provided with the abovementioned substituents $R''_1$ on the nitrogen atom. The introduction of a methyl group is effected by the well-known method of Clarke and Eschweiler, according to which the imino esters are heated with a mixture of formic acid and aqueous formaldehyde.

The 3,3′-iminodipropionic esters can be cyclizised under the influence of a basic condensation agent, such as sodium methoxide or sodium hydride, by boiling the reactants suspended or dissolved in an inert solvent, such as benzene, toluene or dimethyl formamide. The alcohol generated during the reaction, is removed by simultaneous distillation of the mixture. The products of this Dieckmann cyclization are 2-benzyl-4-oxo-5-piperidinecarboxylic esters of formula VIII.

Hydrolysis and decarboxylation of the keto esters of formula VIII to 4-piperidones of formula IX are effected by heating a solution of these compounds in an aqueous, strong inorganic acid whereby the tendency of formation of neutral material as a result of decomposition may be limited by a careful choice of the reaction conditions, which should not be too vigorous. In 6 N hydrochloric acid, the reaction is completed within 30 to 50 minutes and, in 2 N hydrochloric acid, the reaction is completed within 5 hours, whereas, 1 N acid requires a reaction time of 12 hours. The last procedure is the preferred one.

Method 2

In this method, propionic esters, provided with a secondary amino function at the β-position, are acylated with the acid chloride of a mono ester of either a dialkyl malonic acid or a 1,1-cycloalkanedicarboxylic acid to form amido dicarboxylic esters having the formula

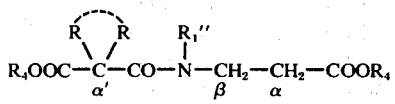

Formula XIII in which both substituents R represent lower alkyl groups, or, in combination with the α' carbon atom, represent a cyclo alkane ring, each $R_4$ represents the same or different alkyl groups and $R''_1$ represents an alkyl or an aralkyl group. These compounds of formula XIII are then submitted to a Dieckmann cyclization to give 2,4-piperidinedione-5-carboxylic esters having the formula

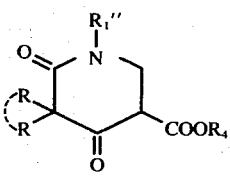

Formula XIV

The products thus obtained are subjected to hydrolysis and then to decarboxylation so as to be converted into 2,4-piperidinediones having the formula

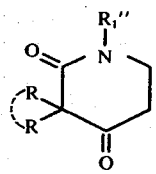

Formula XV

In the diones of formula XV, the 4-oxo group is masked by conversion into a ketal group, which leads to compounds having the formula

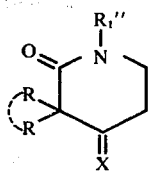

Formula XVI in which X represents the protected oxo group. The 2-piperidones according to formula XVI are subsequently reacted with a benzyl lithium to give 2-benzylidene piperidines having the formula

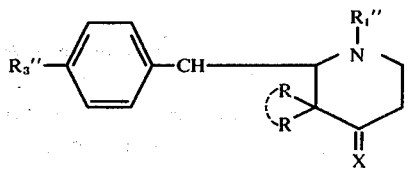

Formula XVII in which $R''_3$ represents a hydrogen atom or an alkoxy group, whereupon the benzylidene group is saturated to a benzyl group and the 4-oxo group is regenerated to give the desired 2-benzyl-4-piperidones having the formula

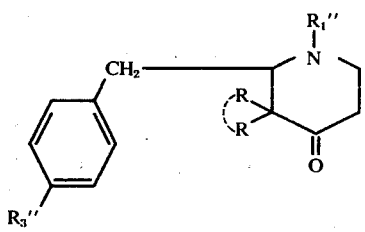

Formula XVIII

The 3,3-dialkyl-2,4-piperidinediones according to formula XV belong to a type which has been described by Schnider et al., for example, in Festschrift Emil Barell 1936, 195; German Patent specification 634,284 and Swiss patent specification 256,347. In these publications, the authors arrived at said compounds by catalytic reduction of the corresponding 2,4(1H,3H)-pyridinediones, which were obtained by a four-step synthesis, starting from 2,2-dialkyl acetoacetic esters.

The route of synthesis of compounds according to formula XV described hereinabove is a new one and seems to be more attractive than the less direct route used by Schnider. The new method consists in a cyclization according to Dieckmann applied to amido dicarboxylic esters according to formula XIII, followed by decarboxylation after hydrolysis of the formed 4,6-dioxo-piperidine-3-carboxylic esters of formula XIV. It may be remarked that the present procedure is reminiscent of the method applied by some authors to the synthesis of certain 1-aralkyl-2,4-piperidine diones which were devoid of further substituents at the piperidine ring or held a methyl or ethyl substituent at position 5, for example, Y. Ban, Pharm. Bull. (Japan) 3, 53 (1955); M. Barash, J.M. Osbond and J.C. Wickens, J. Chem. Soc. 1959, 3530; and A.R. Battersby and J.C. Turner, J. Chem. Soc. 1960, 717.

The Dieckmann cyclization is carried out in the usual manner, namely by heating a solution of the amido dicarboxylic esters in an inert solvent, such as benzene, toluene or dimethyl formamide, in the presence of a basic condensing agent, such as, sodium methoxide, sodium hydride or sodium amide. The alcohol formed is removed continuously during the reaction by distillation.

The saponification and decarboxylation of the cyclization products occur in an aqueous acid medium, for example, 6 N hydrochloric acid, at boiling temperature whereby the reaction is completed within 30 to 50 minutes. Longer reaction times are required if the acid concentration is lower. Too vigorous reaction conditions should be avoided as otherwise the amide function also may be attacked.

The necessary starting materials for the Dieckmann cyclization, such as, the amidodicarboxylic esters of formula XIII are obtained in a simple manner by reaction of 2,2-dialkylmalonic acid mono-ester chlorides or 1-chloroformyl-1-cycloalkanecarboxylic acid esters with $\beta$-alkylamino or $\beta$-aralkylamino propionic esters in a basic medium, for instance in an ethereal solution to which pyridine or triethylamine is added, or in pyridine proper as the solvent.

In order to enable the introduction of a benzyl group at position 2 of compounds according to the formula XV, the keto function at position 4 has to be masked beforehand. For that purpose, this function is converted into a ketal group, preferably an ethylene ketal grouping. These ketals of formula XVI, wherein X is $-O-CH_2-CH_2-O-$, are brought into reaction with benzyl lithium or p-alkoxybenzyl lithium. These lithium compounds are easily accessible according to the method of Gilman by reaction of lithium with benzyl ethyl ether [(H. Gilman et al., J. Org. Chem. 23, 2044 (1958) and 26,3723 (1961)], or according to the invention, with p-methoxybenzyl ethyl ether. A mixture of tetrahydrofuran and ethyl ether is the preferred solvent in this reaction. As a result of the conversion of the lithium compounds with the N-substituted lactam function in Formula XVI, 2-benzylidene-piperidines having the formula XVII (wherein X = $-O-CH_2-CH_2-O-$) are obtained, which are saturated to 2-benzyl-piperidines by means of catalytic hydrogenation.

Regeneration of the 4-oxo group is brought about by hydrolysis of the ketal function. As stated above this hydrolysis should be carried out in an acidic aqueous medium, such as hydrochloric acid, under conditions which are sufficiently controlled in consideration of the limited stability of the desired 2-benzyl-4-piperidones of formula XVIII.

As to the conversion of the 4-piperidones of formulas V, IX or XVIII into the corresponding 4-piperidinols, this can be effected by catalytic hydrogenation, as well as by other methods which are commonly used in the reduction of a carbonyl to a carbinol group.

Complex metal hydrides, such as, sodium borohydride or notably lithium aluminum hydride, are suitable for obtaining 4-piperidinols of formula III in which $R_2=H$. In order to prepare 4-piperidinols in which $R_2=$alkyl, aryl, heteroaryl or aralkyl, the 4-piperidones are brought into reaction with organo metal compounds, preferably lithium compounds. The reaction with methyl lithium, with phenyl lithium and with 2-pyridyl lithium lead smoothly to the desired 4-piperidinols with $R_2=CH_3$, $C_6H_5$ and $2-C_5H_4N$, respectively. However, with ethyl lithium, and more pronounced with propyl lithium, the reaction takes a less complete course and it is advisable to repeat the reaction in order to arrive at higher yields.

Moreover the 4-ethyl-4-piperidinols may be prepared in excellent yields via 4-ethinyl-4-piperidinols which are products of the reaction of the 4-piperidones with a mono alkalimetal salt of acetylene under suitable conditions. These conditions are, for instance, reaction with ethinyl lithium in liquid ammonia, reaction with ethinyl potassium in tertiary butanol at a temperature below zero, or reaction with the complex of ethinyl lithium and ethylenediamine in dimethylformamide at temperatures between zero and room temperature. The 4-ethinyl substituent can be converted into a 4-ethyl group by means of catalytic hydrogenation. In this way 4-ethyl-4-piperidinols may be obtained in a better yield than by the one step reaction with ethyl lithium.

When the 4-piperidinols are prepared from 4-piperidinones, a second asymmetric carbon atom emerges in the piperidine ring and, therefore, the 4-piperidinols may arise in two different racemic forms, both of which equally suit the conversion into the same 6,7-benzomorphan derivatives. As a consequence separation of the racemates is not necessary.

The 2-benzyl-4-piperidinols with $R'_3 =$ hydroxy and the corresponding 4-piperidinones are compounds according to this invention as well as the derivatives in which $R'_3$ has the other defined meanings. Nevertheless, insofar as it is an object of the invention to provide starting materials for the new benzomorphan derivatives, it is irrelevant to prepare the compounds with $R'_3$ = hydroxy separately, as 2-benzyl-4-piperidinols with $R'_3 =$ hydroxy, as well as those with $R'_3 =$ alkoxy, will lead to the same 6,7-benzomorphans by reason of the fact that, under the given reaction conditions, alkoxy substituents usually will be converted into hydroxy groups.

It will be clear that, if an acid chloride of a mono ester of a mono alkyl malonic acid is selected as the starting material, the present synthesis (method 2) will lead to 3-mono alkyl substituted 2-benzyl-4-piperidinols, a type which has been described by H. Henecka et al. in the above-mentioned British patent specification 1,078,286 and which can serve as an intermediate in the preparation of previously known 6,7-benzomorphans.

The invention will now be further illustrated by the following specific, non-limiting examples.

EXAMPLE 1

Methyl 2,2-dimethyl-4-(p-methoxyphenyl)-acetoacetate

To a gently refluxing suspension of 227 g of granulated zinc, activated by the addition of 1 g of iodine, in 500 ml of dry tetrahydrofurane there is dropped with mechanical stirring and under exclusion of moisture, a solution of 700 g of methyl 2-bromoisobutyrate and 540 g of methyl p-methoxy-phenylacetate in 500 ml of tetrahydrofurane. As soon as the reaction has started, apparent from the formation of a turbidity and stronger reflux, the addition is continued at such a rate as to maintain gentle reflux with minimal application of external heating. After all of the solution has been added, stirring and refluxing is continued for 5 hours. Then the reaction mixture is cooled with ice and 1500 ml of 4 N sulphuric acid is added dropwise with vigorous stirring.

The organic layer is separated, after the eventual removal of some solid material by filtration, and the aqueous solution extracted with ether. The combined organic solutions are washed with an aqueous solution of sodium bicarbonate. Evaporation of the solvent leaves the crude ester which is purified by distillation in vacuo. Yield 60 – 65%, boiling point 145° C (1 mm), $n_D^{20}$ 1.5140.

EXAMPLE 2

Methyl 2,2-dimethyl-4-phenyl-acetoacetate

In the same manner, as described in example 1, however, starting from methyl phenylacetate, the above-mentioned compound is prepared. Yield 71%, boiling point 112° C (1 mm), $n_D^{18}$ 1.5043.

EXAMPLE 3

Methyl 3-benzylamino-2,2-dimethyl-4-(p-methoxyphenyl)-butyrate

Titanium tetrachloride (114 g) is dropped over a period of 2 hours to a mixture of 250 g of methyl 2,2-dimethyl-4-(p-methoxyphenyl)-acetoacetate, 384 g of benzylamine and 1000 ml of dry toluene. The mixture is kept in an atmosphere of nitrogen, stirred vigorously and cooled with ice so as to maintain the temperature at 5° – 10° C. Initially the colour of the mixture turns to brownblack but on keeping it at room temperature for 5 days it has taken a light tan appearance. The formed $TiO_2$ and benzylamine hydrochloride are removed by filtration and washed thoroughly with toluene. Evaporation of the combined filtrates leaves 268 g of crude ketimine having a purity of 90%. This corresponds with a yield of circa 70%. Subsequently, the crude Shiff base (920 g), dissolved in 1.25 l of acetic acid is hydrogenated with the aid of 5 g of platinum oxide as a catalyst and at atmospheric pressure. Hydrogen uptake is rapid at first but after absorption of 55 l it slackens down considerably. At that point the hydrogenation is interrupted whereupon the catalyst is removed by filtration and the solution concentrated by evaporation of the solvent in vacuo. The residue is taken up in water and the resulting aqueous solution made alkaline with the aid of 4 N sodium hydroxide. The basic material which separates is taken up in ether. Removal of the solvent by evaporation leaves an oily residue which is dissolved in 700 ml of ethanol. After cooling overnight in the refrigerator a crop of 440 g of coarse crystals has deposited from the solution. Recrystallization from ethanol gives the pure product, melting at 58° – 60° C.

EXAMPLE 4

Methyl 3-benzylamino-2,2-dimethyl-4-phenyl-butyrate

A mixture of 440 g of methyl 2,2-dimethyl-4-phenyl-acetoacetate, 214 g of benzylamine, 500 ml of toluene and 2 ml of boron trifluoride etherate is refluxed under continuous removal of the water formed by azeotropic distillation. After 16 hours, when only one half of the water expected has been separated, 90 g of benzylamine and 2 ml of a solution of hydrogen bromide in acetic acid (45%) are added and refluxing is continued for 25 hours after which the formation of water is completed. The mixture is shaken with an aqueous solution of sodium bicarbonate, dried over magnesium sulphate and distilled at reduced pressure. The fraction with boiling range 147° – 170° C (0.2 mm) consists largely of ketimine (500 g), suited to hydrogenation without further purification. Fractional distillation affords pure ketimine with a boiling range of 149° – 152° C (0.25 mm), $n_D^{20}$ 1.5532. Crude ketimine (500 g), dissolved in 500 ml of acetic acid, is submitted to catalytic hydrogenation at atmospheric pressure and room temperature, and with platinum dioxide (2 g) as a catalyst. Hydrogen uptake stops with 24 l. After removal of the catalyst by filtration, the solvent is evaporated completely in vacuo. The oily residue is dissolved in ca. 250 ml of ethanol. From this solution the above compound separated in coarse crystals. Yield 220 g, melting at 92° – 94° C.

EXAMPLE 5

Methyl 3-amino-2,2-dimethyl-4-(p-methoxyphenyl)-butyrate

The benzylaminoacid ester (440 g), obtained according to example 3, can be easily debenzylated by hydrogenation at atmospheric pressure and room temperature. The solvent is 1.25 l of acetic acid and the catalyst 20 g of 5% palladium on charcoal. After 2 hours hydrogen uptake comes to a standstill, 31 l of hydrogen being absorbed. Processing as described in the preceding example yields a product with a melting point of 46° – 49° C in an overall yield of 35% based on the starting keto ester.

EXAMPLE 6

Methyl 3-amino-2,2-dimethyl-4-phenyl-butyrate

In a similar way as described in example 5 hydrogenolytic debenzylation of methyl 3-benzylamino-2,2-dimethyl-4-phenyl-butyrate affords the above-mentioned compound as an oil which solidifies on standing. Melting point 37+ – 39° C. Yield 34%, based on the amount of methyl 2,2-dimethyl-4-phenyl-acetoacetate used.

EXAMPLE 7

Dimethyl 3-(p-methoxybenzyl)-2,2-N-trimethyl-3,3'-iminodipropionate

A mixture of 351 g of methyl 3-amino-2,2-dimethyl-4-(p-methoxyphenyl)butyrate, 205 g of methyl acrylate and 3 ml of acetic acid is heated in an autoclave during 18 hours at 130° C. The contents is removed from the autoclave with the aid of ether whereupon the volatile material is evaporated at diminished pressure. To the resulting crude reaction product are added dropwise successively 280 ml of formic acid (95%) and 280 ml of aqueous formaldehyde (35%). During this operation, which takes 1.5 hours, the mixture is stirred and cooled with water.

Subsequently, it is warmed at 40° C for 1 hour, kept at room temperature during 16 hours and finally warmed one additional hour at 60° C. After removal of low boiling material by evaporation in vacuo, the resulting oil is treated with chloroform and a concentrated aqueous solution of potassium carbonate. The organic solution is dried over magnesium sulphate and evaporated, leaving an oily residue. Neither this product nor its unmethylated predecessor can be purified by distillation because of extensive decomposition at elevated temperatures.

The first step of the synthesis described in this example may be also carried out at a lower temperature without the use of an autoclave. In this case, a mixture of 450 g of methyl 3-amino-2,2-dimethyl-4-(p-methoxyphenyl)-butyrate and 180 ml of methyl acrylate is stirred at 50° C when 45 ml of acetic acid is added rather rapidly. The temperature of the mixture is raised to 90° C by application of heat and then rises spontaneously to 100° C. After one hour the reaction has ended; the excess of methyl acrylate and acetic acid is removed by evaporation in vacuo at 50° C.

EXAMPLE 8

Methyl 2-(p-methoxybenzyl)-4-oxo-1,3,3-trimethyl-5-piperidine-carboxylate hydrochloride The crude methylimino dipropionic ester prepared according to the method described in example 7 is dissolved in 3 l of dry toluene. Sodium methoxide (157 g) is added and the mixture is stirred and heated in an oil bath at 100° – 110° C. The methanol which is generated during the reaction is removed by azeotropic distillation. It formation comes to an end after two and a half to three hours when merely toluene is distilled. The mixture is cooled whereafter water is added. The toluene layer is washed with water and, after being dried with magnesium sulphate, evaporated in vacuo. The residue, consisting of crude keto ester is treated with an alcoholic solution of hydrogen chloride. The hydrochloride separates as a crystalline precipitate. The yield is 268 g (54%, based on the quantity of starting amino ester described in example 5). Melting point 163° – 164° C (decomp.).

EXAMPLE 9

Methyl 2-(p-methoxybenzyl)-4-oxo-1,3,3-trimethyl-5-piperidine-carboxylate hydrochloride To a solution of 19.0 g of crude methyliminodipropionic acid ester, prepared according to example 7, in 150 ml of dry dimethylformamide, there is added 4.8 g of sodium hydride (50% dispersion in oil), the mixture being stirred and gradually heated until, at about 70° C, a vigorous evolution of hydrogen takes place. The reaction is completed by heating the mixture at 110° – 120° C during three hours. After cooling a solution of 30 g of ammonium chloride in 300 ml of water is added, whereupon the solvents are removed by evaporation in vacuo. The residue is shaken with 1 N hydrochloric acid and benzene. The acidic aqueous layer is made alkaline with an excess of aqueous ammonia and subsequently extracted with chloroform. The organic solution is processed as usually and the product is secured as the hydrochloride. The compound is identical with the one obtained according to example 8. After recrystallization the yield is 49%.

EXAMPLE 10

Ethyl 3,3-dimethyl-2-(p-methoxybenzyl)-4-oxo-5-piperidine-carboxylate hydrochloride In a manner similar to the method described in example 8, however, starting from the addition product of the reaction of ethyl acrylate with methyl 3-amino-2,2-dimethyl-4-(p-methoxyphenyl)-butyrate (prepared according to the method depicted in example 7), the above-mentioned compound is obtained. The yield of the substance amounts to 33%. The melting point, after recrystallizaton from ethanol, is 177° – 180° C.

EXAMPLE 11

Ethyl 2-benzyl-4-oxo-1,3,3-trimethyl-5-piperidinecarboxylate hydrochloride

A mixture of 240 g of methyl 3-amino-2,2-dimethyl-4-phenyl-butyrate, 171 g of ethyl acrylate and 1.5 ml of acetic acid is heated at 130° C for 18 hours. The crude addition product (365 g) is methylated by means of the Clarke-Eschweiler method, as described in example 7. As a result 325 g of an imminodipropionic mixed ester is obtained as an oil. This compound (325 g) is submitted to a Dieckmann cyclization by reaction in toluene with 90 g of sodium methoxide under conditions as described in example 8.

In working up, the reaction mixture is neutralized by the addition, with cooling, of acetic acid and afterwards washed with water and processed as usually. The yield of the hydrochloride is 52%. Recrystallized from ethanol/acetone the compound melts at 180° – 182° C, with decomposition.

EXAMPLE 12

2-(p-Methoxybenzyl)-1,3,3-trimethyl-4-piperidone hydrochloride

A solution of the hydrochloride (80 g) of methyl 2-(p-methoxybenzyl)-4-oxo-1,3,3-trimethyl-5-piperidinecarboxylate in 450 ml of 1 N hydrochloric acid is refluxed for 12 hours. After cooling, some resinous material is removed by extraction with ether. Alkalinization of the aqueus solution with the aid of ammonia causes the separation of the piperidone which is extracted with ether. Concentration in vacuo of the extent gives a residue which is dissolved in ethanolic hydrogen chloride. Evaporation of the ethanol leaves a syrupy residue which is dissolved in acetone, whereafter the crystalline hydrochloride separates. Yield 87%. Melting point 168° – 170° C, with decomposition.

EXAMPLE 13

2-Benzyl-1,3,3-trimethyl-4-piperidone hydrochloride

A solution of 217 g of the hydrochloride of ethyl 2-benzyl-4-oxo-1,3,3-trimethyl-5-piperidine carboxylate in 6 N hydrochloric acid is refluxed for 40 minutes. The piperidone is gathered as the hydrochloride in the same way as described in example 12. Yield 75%; melting point 177° – 179° C, with decomposition.

EXAMPLE 14

3,3-Dimethyl-2-(p-methoxybenzyl)-4-piperidone hydrochloride

In a manner similar to the one described in example 12, however, starting from ethyl 2-(p-methoxybenzyl)-3,3-dimethyl-4-oxo-5-piperidine-carboxylate, the above-mentioned compound is obtained in a yield of 75%. After recrystallization from ethanol/ethyl ether, the substance melts at 212° – 213° C, with decomposition.

EXAMPLE 15

3,3-Dimethyl-2-(p-methoxybenzyl)-4-piperidone hydrochloride

Starting from 19.1 g of crude 3-(p-methoxybenzyl)-2,2-dimethyl-3,3'-imino-dipropionic acid dimethyl ester (obtained from the addition-reaction of methyl acrylate with 3-amino-2,2-dimethyl-4-(p-methoxyphenyl)-butyric acid methyl ester), dissolved in 150 ml of dry dimethylformamide and in the presence of 7.2 g of sodiumhydride (50% dispersion in oil), a Dieckmann condensation is carried out as described in example 9. The crude condensation-product is hydrolyzed and decarboxylated as described in example 12, giving the desired piperidone in an overall yield of 44%.

EXAMPLE 16

1-Benzyl-3,3-dimethyl-2-(p-methoxybenzyl)-4-piperidone hydrochloride

A mixture of 24.5 g of crude dimethyl 2,2-dimethyl-3-(p-methoxybenzyl)-3,3'-iminodipropionate, 27 g of benzyl chloride, 23 g of potassium iodide, 40 g of potassium carbonate and 300 ml of methyl ethyl ketone is refluxed and stirred during 35 hours. The mixture is cooled and evaporated in vacuo whereupon the residue is treated with chloroform. Inorganic material is removed by filtration and the filtrate is concentrated in vacuo leaving a residue which is shaken with 300 ml of 4 N hydrochloric acid and 100 ml of petroleum ether in order to remove neutral products. After basification with aqueous ammonia, the N-benzyl-2,2-dimethyl-3-(p-methoxybenzyl)-3,3'-iminodipropionic acid dimethylester is extracted from the mixture by shaking with chloroform. It is obtained in nearly quantitative yield, and, without purification submitted to a Dieckmann cyclization using 5.2 g of sodium hydride (50% dispersion in oil) and 200 ml of dimethylformamide. Further processing is carried out according to the directions already described in preceding examples, giving the above-mentioned product which is recrystalized from ethanol/ether. Yield 35%. Melting point 161° – 162° C, with decomposition.

EXAMPLE 17

Diethyl 3-oxo-2,2,N-trimethyl-3,3'-iminodipropionate

To a solution of 61 g of N-methyl-β-alanine ethyl ester in 600 ml of dry pyridine there is added 82 g of ethyl 2-chloroformyl-2-methylpropionate. During the addition, which takes 30 minutes, the mixture is mechanically stirred and cooled with ice. Stirring is continued at 10° C for 30 minutes and then at 30° – 40° C for 1 hour. Next the pyridine is evaporated in vacuo, leaving a residue to which a small quantity of water is added, whereafter the mixture is extracted with ether. The extract is dried over magnesium sulphate and evaporated leaving the above-mentioned product as a liquid which is purified by distillation at reduced pressure. Yield 97 g (75%). Boiling point 134° – 136° C (1 mm). $n_D^{22}$ 1.4565.

EXAMPLE 18

Dimethyl 2,2-diethyl-N-methyl-3-oxo-3,3'-iminodipropionate

To a solution of 19.2 g of methyl 2-chloroformyl-2-ethyl-butyrate and 20 g of triethylamine in 100 ml of dry ether, which is mechanically stirred and cooled at −10° C, there is added dropwise 12.8 g of N-methyl-β-alanine methyl ester dissolved in 50 ml of dry ether. After the addition, which takes 30 minutes, the mixture is stirred during 18 hours at room temperature. After filtration of the separated triethylamine hydrochloride, the solvent is evaporated leaving the desired product as an oil, boiling at 118° C (0.2 mm). Yield 93%. $n_D^{19}$ 1.4646.

EXAMPLE 19

Diethyl N-methyl-3-oxo-2,2-tetramethylene-3,3'-iminodipropionate

In a similar manner as described in example 18, however, starting from 83.9 g of 1-chloroformyl-1-cyclopentane-carboxylic acid ethyl ester, 59 g of N-methyyl-β-alanine ethylester and 83 g of triethylamine, the above-mentioned compound is obtained. Yield 81%. Boiling point 129° – 133° C (0.3 mm).

EXAMPLE 20

Diethyl N-methyl-3-oxo-2,2-pentamethylene-3,3'-iminodipropionate

In a similar manner as described in example 18, however, starting from 39.6 g of 1-chloroformyl-1-cyclohexanecarboxylic acid ethyl ester, 24 g of N-methyl-β-alanine ethyl ester and 36 g of triethylamine, the above-mentioned compound is obtained. Yield 84%. Boiling point 166° – 169° C (1 – 1.5 mm).

EXAMPLE 21

Diethyl N-benzyl-2,2-dimethyl-3-oxo-3,3'-iminodipropionate

In a similar manner as described in example 18, however, applying N-benzyl-β-alanine ethyl ester, the above compound is obtained. Yield 76%. Boiling point 184° – 190° C (0.3 – 0.4 mm).

EXAMPLE 22

1,3,3-Trimethyl-2,4-piperidinedione

A mixture of 97 g of diethyl 3-oxo-2,2,N-trimethyl-3,3'-iminodipropionate, 450 ml of toluene and 42 g of sodium methoxide is stirred mechanically and boiled under continuous removal of ethanol formed by means of azeotropic distillation. After 3 hours, when the boiling point of toluene is reached, the mixture is cooled and made weakly acidic with the aid of 4 N hydrochloric acid.

The toluene layer is washed with water and the aqueous solutions are extracted three times with ether. After drying over magnesium sulphate the combined organic solutions are stripped of the solvents by evaporation in vacuo. To the crude condensation product which is left as an oil, 300 ml of hot 6 N hydrochloric acid is added and the resulting solution is refluxed for 40 minutes. After rapid cooling, the mixture is made alkaline withe the aid of aqueous ammonia and then extracted with chloroform. The extract is dried over magnesium sulphate and evaporated in vacuo.

The product is purified by distillation. Yield 64%. Boiling point 93° – 98° C (1 mm). It solidifies, and melts at 39° – 42° C after recrystallization from petroleum ether.

EXAMPLE 23

3,3-Diethyl-1-methyl-2,4-piperidinedione

In a manner similar to the method described in example 22, however, starting from dimethyl 2,2-diethyl-N-methyl-3-oxo-3,3'-iminodipropionate, the above-mentioned compound is obtained. Yield 75%. Boiling point 102° – 104° C (0.2 – 0.3 mm). $n_D^{17}$ 1.4850.

EXAMPLE 24

1-Benzyl-3,3-dimethyl-2,4-piperidinedione

In a manner similar to the method described in example 22, however, starting from diethyl N-benzyl-2,2-dimethyl-3-oxo-3,3'-iminodipropionate, the above-mentioned compound is obtained. Yield 44%. The product melts at 68° – 70° C (crystallized from petroleum ether).

EXAMPLE 25

7-Methyl-7-azaspiro [4.5] decane-6,10-dione

A boiling mixture of 700 ml of toluene, 94.4 g of diethyl N-methyl-3-oxo-2,2-tetramethylene-3,3'-iminodipropionate and 40 g of sodium methoxide is stirred mechanically while the ethanol generated during the reaction is removed by azeotropic distillation. After 3 hours the boiling point of toluene has been reached, 300 ml of distillate being collected. After the addition of 60 g of ammonium chloride, stirring is continued for another 30 minutes when, after cooling, water is added. The organic solution is separated, dried and evaporated in vacuo. The residue (77 g) is hydrolyzed and decarboxylated by means of heating at 95° C with 300 ml of 1 N hydrochloric acid during 18 hours. Processing as described in example 22 gives the above-mentioned product. Yield 48%. Boiling point 138°–145° C (1.5 –2 mm).

EXAMPLE 26

2-Methyl-2-azaspiro [5.5] undecane-1,5-dione

In a manner similar to the method described in example 25, diethyl N-methyl-3-oxo-2,2-pentamethylene-3,3'-iminodipropionate (43.2 g) dissolved in 250 ml of toluene, is submitted to the Dieckmann cyclization, using 17 g of sodium methoxide.

The condensation product (34 g) is saponified and decarboxylated as described in the preceding example. The desired product is obtained in a 45% yield. Boiling point 110°–130° C (0.7 mm).

EXAMPLE 27

6,6,8-Trimethyl-1,4-dioxa-8-azaspiro [4.5] decan-7-one

This ketal is prepared by refluxing a solution of 6.5 g of 1,3,3-trimethyl-2,4-piperidinedione, 5 g of ethylene glycol and 30 mg of p-toluenesulphonic acid in 45 ml of benzene during 19 hours. The water formed is separated with the aid of a Dean-Stark trap. After shaking the solution with saturated aqueous sodium bicarbonate, it is dried over magnesium sulphate, whereafter the solvent is evaporated in vacuo. The residue is recrystallized from petroleum ether. Yield 5 g. Melting point 69°–72° C. From the mother liquor an additional 1.7 g (mp 66°–71° C) can be obtained.

EXAMPLE 28

6,6-Diethyl-8-methyl-1,4-dioxa-8-azaspiro [4.5] decan-7-one

In a manner similar to the method described in example 27, however, starting from 3,3-diethyl-1-methyl-2,4-piperidinedione, the above ketal is obtained in a yield of 82%. In order to arrive at this high yield the reaction time has to be protracted to 120 hours. Boiling point 99°–103° C (0.1 mm). $n_D^{19}$ 1.4972.

EXAMPLE 29

8-Benzyl-6,6-dimethyl-1,4-dioxa-8-azaspiro [4.5] decan-7-one

In a manner similar to the method described in example 27, however, applying 1-benzyl-3,3-dimethyl-2,4-piperidinedione, the above-mentioned ketal is obtained in a 86% yield. After recrystallization from petroleum ether it melts at 77°–79° C.

EXAMPLE 30

12-Methyl-1,4-dioxa-12-azadispiro [4.0.4.4] tetradecan-11-one

A solution of 26 g of 7-methyl-7-azaspiro [4.5] decane-6,10-dione in 150 ml of ethylene glycol, containing 100 mg of p-toluenesulphonic acid, is distilled at atmospheric pressure until 110 ml of distillate has been collected. The distillation residue is then shaken with ether and dilute aqueous ammonia. The aqueous layer is extracted with chloroform and the combined organic solutions are dried and evaporated in vacuo. The residue is recrystallized from ether. Melting point 84 –85° C. Yield 56%.

EXAMPLE 31

13-Methyl-1,4-dioxa-13-azadispiro [4.0.5.4] pentadecan-12-one

In a manner similar to the method decribed in example 30, the above ketal is prepared from 12.9 g of 2-methyl-2-azaspiro [5.5] undecane-1,5-dione. Yield 50%. Melting point 91°–92° C (recrystallized from ether).

EXAMPLE 32

2-(p-Methoxybenzyl)-1,3,3-trimethyl-4-piperidone hydrochloride

A solution of p-methoxybenzyl lithium is prepared according to the directions given by Gilman, et al. for the preparation of benzyl lithium. To this purpose 1.4 g of lithium wire, cut into small pieces, is suspended in 20 ml of dry peroxide free tetrahydrofuran. Under cooling (−10° C), mechanical stirring and flushing with nitrogen, there is added 0.5 ml of a solution of p-methoxybenzyl ethyl ether in absolute ether (5 g dissolved in 15 ml of ether). After 1–1.5 hour the reaction starts, which is recognisable by the development of a yellow-orange colour. Then the remainder of the ethereal solution is added dropwise with cooling (−10° C) over a period of 2 hours.

Cooling and stirring are continued for an additional 18 hours whereafter the p-methoxybenzyl lithium contents of the brown-red solution is determined by titration as described by Gilman. To a mechanically stirred and nitrogen flushed ethereal solution (15 ml) of 1.5 g of 6,6,8-trimethyl-1,4-dioxa-8-azaspiro [4.5] decan-7-one which is cooled in ice, there is added dropwise 40 ml of a 0.2 molar solution of p-methoxybenzyl lithium, as prepared above. The addition lasts 1 hour whereafter, under continuous stirring, the mixture is allowed to come to room temperature gradually (16 hours). Water is added (cooling with ice) and the organic layer is washed three times with water. After drying and evaporation in vacuo, a yellow oil (3.5 g) is obtained. The infrared spectrum (in carbon tetrachloride) demonstrates the absence of starting material (absence of the amide carbonyl band at 6.08 μ) and the presence of the reaction product by a strong band at 6.2μ (conjugated C = C). The oil is dissolved in 75 ml of ethanol and submitted to catalytic hydrogenation, with platinum oxide as the catalst, at room temperature and normal pressure. Hydrogen absorption stops after an uptake of 130 ml.

After filtration the solution is concentrated in vacuo. The colourless oil which remains, is dissolved in 30 ml of 2 N hydrochloric acid and the solution is heated on the steam bath for 20 minutes to bring about the hydrolysis of the ketal function. After cooling, the mixture is made alkaline and extracted three times with ether. The extract is processed as usual. The product is secured as the hydrochloride which is recrystallized from ethanol/acetone. Yield 31%. Melting point 173°–175° C, with decomposition. As shown by the infrared spectra this product is identical with the one obtained according to Example 12.

EXAMPLE 33

1-Benzyl-3,3-dimethyl-2-(p-methoxybenzyl)-4-piperidone hydrochloride

In a manner similar to the method described in example 32, however, starting from 8-benzyl-6,6-dimethyl-1,4-dioxa-8-azaspiro [4.5] decan-7-one, the above compound is obtained in a yield of 14%. After recrystallization from ethanol/ether, the compound melts at 156°–157° C, with decomposition. As is shown by the infrared spectra this product is identical with the one obtained according to example 16.

EXAMPLE 34

2-Benzyl-1,3,3-trimethyl-4-piperidone hydrochloride

In a manner similar to the method described in example 32, however, applying a solution of benzyl lithium instead of p-methoxybenzyl lithium, the above product is obtained in a 88% yield. Melting point 176°–179° C, with decomposition.

EXAMPLE 35

2-Benzyl-3,3-diethyl-1-methyl-4-piperidone hydrochloride

In a manner similar to the method described in example 32, however, using benzyl lithium and 6,6-diethyl-8-methyl-1,4-dioxa-8-azaspiro [4.5] decan-7-one as the reactants, the above-mentioned compound is obtained in a yield of 63%. After recrystallization from ethanol/ether the product melts at 163°–164° C, with decomposition.

EXAMPLE 36

6-(p-Methoxybenzyl)-7-methyl-7-azaspiro [4.5] decan-10-one hydrochloride

In a manner similar to the method described in example 32, however, starting from 12-methyl-1,4-dioxa-12-azadispiro [4.0.4.4 tetradecan-11-one the above compound is obtained in the form of the free base. It is isolated as the picrate, melting at 180°–181° C. Yield 90%. From the picrate, via the free base, the hydrochloride can be prepared. Melting point 166°–167° C, with decomposition.

EXAMPLE 37

6-Benzyl-7-methyl-7-azaspiro [4.5] decan-10-one hydrochloride

In a manner similar to the method described in example 32, however, starting from 12-methyl-1,4-dioxa-12-azadispiro [4.0.4.4] tetradecan-11-one, which in this case is reacted with benzyl lithium, the abovementioned compound is obtained. Yield 59%. After recrystallization from ethanol/acetone the substance melts at 156°–157° C.

EXAMPLE 38

1-Benzyl-2-methyl-2-azaspiro [5.5] undecan-5-one hydrobromide

In a manner similar to the method described in example 32, however, starting from 13-methyl-1,4-dioxa-13-azadispiro [4.0.5.4] pentadecan-12-one, which in this case is reacted with benzyl lithium, the abovementioned compound is obtained in the form of the free base. The product is isolated as the hydrobromide with a melting point of 155°–156° C. Yield 41%.

EXAMPLE 39

2-(p-Methoxybenzyl)-1,3,3,4-tetramethyl-4-piperidinol

To a mechanically stirred and nitrogen flushed ethereal solution (200 ml) of methyl lithium (prepared in the usual manner from 43 g of methyl iodide and 4.8 g of lithium) there is added in small quantities 9 g of 2-(p-methoxybenzyl)-1,3,3-trimethyl-4-piperidone hydrochloride. During the addition, which takes some 1.5 hour, the mixture is cooled with water. It is stirred at room temperature for 16 hours and finally refluxed for 1 hour. Then the lithium compounds are hydrolysed by careful addition of water (cooling with ice) and the basic material is extracted from the mixture with the aid of 4 N hydrochloric acid. Basification of the aqueous solution followed by extraction with ether and processing of the ethereal solution as usual, gives crystals which after recrystallization from petroleum ether melt at 55°–65° C. Yield 84%. Evidently a mixture of epimeric piperidinols has been formed.

EXAMPLE 40

2-(p-Methoxybenzyl)-3,3,4-trimethyl-4-piperidinol hydrochloride

In a manner similar to the method described in example 39, however, starting from 3,3-dimethyl-2-(p-methoxybenzyl)-4-piperidone hydrochloride, the above-mentioned compound is obtained. The substance is secured as the hydrochloride which crystallizes from a mixture of ethanol and ether. Melting point 211°–213° C with decomposition. Yield 5%.

EXAMPLE 41

4-Ethyl-2-(p-methoxybenzyl)-1,3,3-trimethyl-4-piperidinol hydrochloride

The hydrochloride (18 g) of 2-(p-methoxybenzyl)-1,3,3-trimethyl-4-piperidone is converted to the free base by shaking with ether and aqueous sodium hydroxide, followed by evaporation of the ethereal solution. The oily base is dissolved in 30 ml of absolute ether and subsequently reacted with ethyl lithium (3.6 g in 300 ml of benzene) under conditions as described in example 39. According to gaschromatographic examination, conversion to the piperidinol occurs to the extent of only 25 percent. After the addition of water the reaction mixture is worked up as described in example 39 and the crude mixture of piperidone and piperidonal so obtained is treated again with ethyl lithium (2.7 g in 250 ml of benzene). This procedure is repeated once more whereafter still 20 percent of the piperidone appears to be present. Processing as usually furnishes 19 g of an oily base, which is converted to the hydrochloride with the aid of ethanolic hydrogen chloride. After the addition of acetone and ether, 9 g of the above crystalline product separates. Yield 45%. Melting point 232 –234° C with decomposition.

EXAMPLE 42

2-(p-Methoxybenzyl)-4-propyl-1,3,3-trimethyl-4-piperidinol

In a manner similar to the method described in example 41, however, applying n-propyl lithium instead of ethyl lithium, the above-mentioned compound is obtained in a 31% yield. After recrystallization from petroleum ether the substance melts at 85°–102° C.

EXAMPLE 43

2-Benzyl-1,3,3,4-tetramethyl-4-piperidinol

In a manner similar to the method described in example 39, however, starting from 2-benzyl-1,3,3-trimethyl-4-piperidone hydrochloride, the above-mentioned compound is obtained. Yield 69%. After recrystallization from light petrol, the substance melts at 95°–103° C.

EXAMPLE 44

2-Benzyl-4-ethyl-1,3,3-trimethyl-4-piperidinol hydrochloride

In a manner similar to the method described in example 41, however, starting from 2-benzyl-1,3,3-trimethyl-4-piperidone hydrochloride, the above compound is obtained as the hydrochloride, melting at 238°–240° C with decomposition. Yield 45%.

EXAMPLE 45

2-Benzyl-4-ethyl-1,3,3-trimethyl-4-piperidinol hydrochloride

A solution of 4.4 g of 2-benzyl-1,3,3-trimethyl-4-piperidone in 30 ml of absolute ether is added at room temperature and over a period of one hour to a Grignard reagent prepared from 1.1 g of magensium, 5.5 g of ethyl bromide and 35 ml of absolute ether.

After the mixture has been stirred at room temperature during 2 days, it is cooled with ice, whereupon 25 ml of water is added. The etheral solution is dried and acidified by means of ethanolic hydrogen chloride. The substance crystallizes as the hydrochloride, melting at 220°–230° C with decomposition. Yield 13%.

EXAMPLE 46

2-Benzyl-1,3,3-trimethyl-4-piperidinol hydrochloride

A solution of 9 g of 2-benzyl-1,3,3-trimethyl-4-piperidone hydrochloride in 50 ml of methanol is submitted to catalytic hydrogenation at room temperature and atmospheric pressure, with 0.4 g platinum oxide as the catalyst. The product is crystallized from ethanol/ether. Yield 98%. Melting point, after recrystallization, 213°–222° C.

EXAMPLE 47

4-Ethinyl-2-(p-methoxybenzyl)-1,3,3-trimethyl-4-piperidinol

A stream of acetylene, after successively having been washed with water, cooled to −80° C and dried with $CaCl_2$, is led into a mechanically stirred solution of 7 g of lithium in 750 ml of dry liquid ammonia which is cooled at about −50° C. After about 5 hours the blue colour disappears. To the solution of acetylene lithium so obtained there is added dropwise 60 g of 2-(p-methoxybenzyl)-1,3,3-trimethyl-4-piperidone dissolved in 250 ml of absolute ether. During the addition a slow stream of acetylene is maintained, but afterwards this is stopped and the reaction mixture is stirred for 16 hours, the ammonia being allowed to evaporate gradually. The resulting suspension is diluted by addition of 250 ml of absolute ether and stirred for another 2 hours at 30° C. After cooling 54 g of ammonium chloride and water are added. The reaction product is secured from the organic layer in the usual manner. It is recrystallized from a mixture of benzene and petroleum ether. Yield 88%. Melting point 103°–110° C.

EXAMPLE 48

4-Ethinyl-2-(p-methoxybenzyl)-1,3,3-trimethyl-4-piperidinol

Potassium (23.8 g) is dissolved in 500 ml of dry tertiary butanol whereupon 500 ml of absolute ether is added. This solution is cooled with ice and saturated with dry acetylene (cf. example 47).

Then, in the course of 45 minutes, a solution of 59.5 g of 2-(p-methoxybenzyl)-1,3,3-trimethyl-4-piperidone in 250 ml of absolute ether is added dropwise, the mixture being cooled at −10° to −15° C and stirred mechanically. Meanwhile the mixture is flushed with acetylene, which is continued for an additional 3 hours (at −10° C).

Then the reaction mixture is allowed to come to room temperature in the course of 16 hours. After the addition of 53.5 g ammonium chloride, stirring is continued for 30 minutes when 500 ml of ice-cold water is added. The organic solution is separated, dried and evaporated, leaving the desired product as a crystalline residue melting at 103°–110° C. Yield 98%.

EXAMPLE 49

4-Ethyl-2-(p-methoxybenzyl)-1,3,3-trimethyl-4-piperidinol

A solution of 56 g of 4-ethinyl-2-(p-methoxybenzyl)-1,3,3-trimethyl-4-piperidinol in 350 ml of methanol is subjected to hydrogenation at atmospheric pressure and room temperature, the catalyst being 5% palladium on charcoal (5 g.).

Absorption of 8.8 l of hydrogen takes place within 2 hours. Removal of the catalyst by filtration and evaporation of the ethanol in vacuo leaves 55 g of an oil, which solidifies completely. Yield 98%. Melting point 90°–95° C.

EXAMPLE 50

2-(p-Methoxybenzyl)-4-phenyl-1,3,3-trimethyl-4-piperidinol

In a manner similar to the method described in example 41, however, applying phenyl lithium instead of ethyl lithium, the above-mentioned compound is prepared. Yield 88%. Melting point 122°–124° C (after recrystallization from petroleum ether).

EXAMPLE 51

1-Benzyl-2-(p-methoxybenzyl)-3,3,4-trimethyl-4-piperidinol hydrochloride

In a manner similar to the method described in example 39, however, starting from 1-benzyl-2-(p-methoxybenzyl)-3,3-dimethyl-4-piperidone hydrochloride, the above compound is obtained. Yield 43%. Melting point, after recrystallization from ethanol/ether, 213°–214° C (decomp.).

EXAMPLE 52

2-Benzyl-3,3-diethyl-1-methyl-4-piperidinol

To a solution of 6.4 g of 2-benzyl-3,3-diethyl-1-methyl-4-piperidone in 100 ml of ether, there is added within a few minutes, 0.9 g of lithium aluminum hydride. The mixture is stirred at room temperature during four hours. After the addition of 5 g of ammonium chloride stirring is continued for half an hour. The the mixture is washed with 100 ml of water and the ethereal solution is evaporated in vacuo.

The residue is submitted to chromatography on aluminum oxide, a mixture of benzene-ethanol (98 : 2) being the eluent. The product, which shows no tendency to crystallization, is a mixture of two stereoisomers. They can be separated easily by way of the picrates. Fractional crystallization of 6.5 g of a mixture of a picrates gives 2.7 g of a picrate, melting at 206°–208° C, which is sparingly soluble in ethanol, and 2.7 g of an easily soluble picrate which melts at 162°–164° C. From the picrates the isomeric bases can be obtained as oils. If submitted to the cyclization procedure described in example 58, both isomers give rise to the same product.

EXAMPLE 53

2-(p-Methoxybenzyl)-4-(2-pyridyl)-1,3,3-trimethyl-4-piperidinol dihydrochloride

In a manner similar to the method described in example 41, however, applying 2-pyridyl lithium instead of ethyl lithium, the above-mentioned compound is obtained. Yield 68%. The dihydrochloride is hygroscopic and melts at 193°–196° C with decomposition.

EXAMPLE 54

10-Ethyl-6-(p-methoxybenzyl)-7-methyl-7-azaspiro [4.5] decan-10-ol hydrochloride In a manner similar to the method described in example 47, 4.5 g of 6-(p-methoxybenzyl)-7-methyl-7-azaspiro [4.5] decan-10-one (obtained from 8 g of the picrate described in example 36) is reacted with acetylene lithium, prepared by dissolution of 1.1 g of lithium in 200 ml of liquid ammonia saturated with acetylene. The crude reaction product, 10-ethinyl-6-(p-methoxybenzyl)-7-methyl-7-azaspiro [4.5] decan-10-ol, is submitted to catalytic hydrogenation in the usual manner, giving the above-mentioned compound. The hydrochloride melts at 217°–220° C with decomposition. Yield 76%.

EXAMPLE 55

6-Benzyl-10-ethyl-7-methyl-7-azaspiro [4.5] decan-10-ol hydrochloride

In a manner similar to the method described in example 47, 2 g of 6-benzyl-7-methyl-7-azaspiro [4.5] decan-10-one hydrochloride is reacted in 100 ml of liquid ammonia with acetylene lithium (from 0.5 g of lithium). The reaction product, 6-benzyl-10-ethinyl-7-methyl-7-azaspiro [4.5] decan-10-ol (2.0 g), is reduced catalytically. Thus 1.8 g of the abovementioned compound is obtained. It is converted into the hydrochloride which melts at 228°–230° C. Yield 55%.

EXAMPLE 56

1-Benzyl-2-methyl-2-azaspiro [5.5] undecan-5-ol picrate

To a solution of 0.28 g of 1-benzyl-2-methyl-2-azaspiro [5.5] undecan-5-one in 20 ml of absolute ether there is added, with stirring and at room temperature, 0.04 g of lithium aluminium hydride. After 45 minutes a small quantity of ammonium chloride and water is added. The ethereal solution is dried and evaporated in vacuo. The residue does not crystallize. It is converted into the picrate which melts at 205°–206° C. Yield 94%.

EXAMPLE 57

1-Benzyl-3,3-dimethyl-4-ethyl-2-(p-methoxybenzyl)-4-piperidinol hydrochloride

In a manner similar to the method described in example 47, 5 g of 1-benzyl-3,3-dimethyl-2-(p-methoxybenzyl)-4-piperidone is reacted with acetylene lithium (prepared from 1 g of lithium in 75 ml of liquid ammonia). The crude product from this reaction is reduced catalytically as described before, leading to the abovementioned compound which is secured as the hydrochloride. Yield 55%. Melting point 171° – 172° C with decomposition.

EXAMPLE 58

2'-Hydroxy-2,5,9,9-tetramethyl-6,7-benzomorphan

A mixture of 7 g of 2-(p-methoxybenzyl)-1,3,3,4-tetramethyl-4-piperidinol and 70 ml of phosphoric acid (89%) is heated at 180° – 185° C during 16 hours. After cooling the reaction mixture is made alkaline with the aid of aqueous ammonia and subsequently extracted with chloroform. The extract is dried over magnesium sulphate and evaporated, leaving a solid residue which after recrystallization from methyl ethyl ketone melts at 157° – 161° C, with sintering at 153° C. Yield 48%. The hydrochloride melts at 180° – 183° C with decomposition.

EXAMPLE 59

5-Ethyl-2'-hydroxy-2,9,9-trimethyl-6,7-benzomorphan

In a manner similar to the method described in example 58, however, applying 4-ethyl-2-(p-methoxybenzyl)-1,3,3-trimethyl-4-piperidinol, the above product is obtained in a 46% yield. After recrystallization from methyl ethyl ketone the compound melts at 177° – 181° C.

EXAMPLE 60

5-Ethyl-2'-hydroxy-2,9,9-trimethyl-6,7-benzomorphan

A solution of 65 g of 4-ethyl-2-(p-methoxybenzyl)-1,3,3-trimethyl-4-piperidinol in 700 ml of hydrobromic acid (48%) is refluxed during 48 hours. The mixture is diluted with 500 ml of water, filtered and then concentrated in vacuo. The residual sirup is treated with an excess of warm aqueous ammonia. On cooling, a precipitate is formed which is collected by filtration, washed once with water and 3 times with cold acetone. Yield 40%. Melting point 173° – 177° C.

EXAMPLE 61

2'-Hydroxy-5-propyl-2,9,9-trimethyl-6,7-benzomorphan hydrochloride

In a manner similar to the method described in example 58, however, applying 2-(p-methoxybenzyl)-4-propyl-1,3,3-trimethyl-4-piperidinol, the above-mentioned compound is obtained. Yield 24%. Melting point 235° – 245° C, with decomposition.

EXAMPLE 62

2'-Hydroxy-5-phenyl-2,9,9-trimethyl-6,7-benzomorphan

In a manner similar to the method described in example 58, however starting from 2-(p-methoxybenzyl)-4-phenyl-1,3,3-trimethyl-4-piperidinol, the above compound is obtained. Yield 49%. Melting point 223° – 230° C.

EXAMPLE 63

2'-Hydroxy-5-(2-pyridyl)-2,9,9-trimethyl-6,7-benzomorphan dihydrobromide

In a manner similar to the method described in example 59, however, starting from 2-(p-methoxybenzyl)-4-(2-pyridyl)-1,3,3-trimethyl-4-piperidinol dihydrochloride, the above-mentioned compound is obtained. It is purified as the dihydrobromide. Melting point 230° – 233° C (decomposition), after recrystallization from isopropanol. Yield 40%.

EXAMPLE 64

2,5,9,9-Tetramethyl-6,7-benzomorphan hydrochloride

In a manner similar to the method described in example 58, however, starting from 2-benzyl-1,3,3,4-tetramethyl-4-piperidinol, the above compound is obtained. Yield 45%. Melting point 222° – 226° C.

EXAMPLE 65

5-Ethyl-2,9,9-trimethyl-6,7-benzomorphan hydrochloride

In a manner similar to the method described in example 58, however, starting from 2-benzyl-4-ethyl-1,3,3-trimethyl-4-piperidinol, the above-mentioned compound is obtained. Yield 62%. Melting point 224° – 226° C.

EXAMPLE 66

5-Ethyl-2'-hydroxy-2-methyl-9,9-tetramethylene-6,7-benzomorphan oxalate

In a manner similar to the method described in example 58, however, starting from 10-ethyl-6-(p-methoxybenzyl)-7-methyl-7-azaspiro [4.5] decan-10-ol, the above-mentioned compound is prepared. For the purpose of purification, the substance is converted into the O - acetyl compound by boiling with acetic anhydride. After evaporation the solution to dryness, the dark residue is extracted with petroleum ether (boiling point 80° – 100° C). The extract is evaporated in vacuo and the residue is boiled with 1 N hydrochloric acid for 2 hours. After alkalinization with ammonia the benzomorphan separates as an oil, which is extracted from the mixture by shaking with chloroform. Evaporation of the extract leaves the above-mentioned substance. It gives a crystalline oxalate melting at 206° – 208° C. Yield 3%.

EXAMPLE 67

5-Ethyl-2-methyl-9,9-tetramethylene-6,7-benzomorphan hydrochloride

In a manner similar to the method described in example 58, however, starting from 6-benzyl-10-ethyl-7-methyl-7-azaspiro [4.5] decan-10-ol, the above-mentioned compound is obtained. The crude product is purified by chromatography on aluminium oxide with benzene as the eluent and finally secured as the hydrochloride. Melting point 241° – 244° C with decomposition. Yield 18%.

EXAMPLE 68

2'-Hydroxy-2,5,9,9-tetramethyl-6,7-benzomorphan

This substance of which already one method of preparation has been given in example 58, can also be prepared in a different way, which has been described for 9-monosubstituted benzomorphans by Eddy et al., cf. J. Org. Chem. 22, 1370 (1957). The procedure is as follows: A solution of 2,5,9,9-tetramethyl-6,7-benzomorphan in 15 ml of acetic acid is added dropwise to a mixture of 31 ml of nitric acid (100%) and 18 ml of acetic acid, which is stirred mechanically and cooled with ice. After completion of the addition which takes 1.5 hours, the mixture is stirred overnight and allowed to come to room temperature, whereupon it is concentrated in vacuo at 55° C.

The residue is poured on ice, the solution so obtained is made alkaline with ammonia and subsequently extracted with chloroform. Evaporation of the extract gives an amorphous nitro product which is converted into the crystalline hydrochloride of 2'-nitro-2,5,9,9-tetramehtyl-6,7-benzomorphan. Melting point 230° – 232° C, with decomposition, Yield 66%. This nitro compound (1.8 g) is dissolved in 50 ml of methanol and reduced catalytically at atmospheric pressure with 0.7 g of 5% palladium on barium sulphate as the catalyst.

The catalyst is filtered off and the filtrate evaporated in vacuo leaving a residue which is dissolved in 13 ml of 3 N sulphuric acid. To this solution, while stirred and cooled with ice, 0.45 g of sodium nitrite dissolved in 3 ml of water is added in the course of 30 minutes. Then the reaction mixture is heated to 60° C whereupon aqueous sulphuric acid (obtained by mixing 7.5 ml of concentrated acid with 7.5 ml of water) is added dropwise in the course of 30 minutes. Stirring is continued for an additional hour, during which the temperature is raised gradually to 80° C. After cooling by addition of ice the mixture is made alkaline with ammonia and subsequently extracted with chloroform. From this extract the hydroxybenzomorphan derivative can be obtained as described in example 58. After recrystallization from a mixture of ethanol, acetone and ether the yield amounts to 0.7 g (33%). The melting point is 185°

EXAMPLE 69

9.9-Dimethyl-5-ethyl-2'-hydroxy-6,7-benzomorphan

A mixture of 13.5 g of 5-ethyl-2'-hydroxy-2,9,9-trimethyl-6,7-benzomorphan and 52 ml of acetic anhydride is heated at 100° C for 45 minutes. After cooling, the solution is poured on ice, and after careful basification with 50% of aqueous potassium hydroxide, the O-acetyl derivative is secured by extraction with ether. The product is dissolved in 75 ml of dry chloroform, whereupon in the course of 30 minutes a solution of 8 g of cyanogen bromide in 50 ml of dry chloroform is added dropwise with stirring and at room temperature. Stirring is continued for 3 hours at reflux temperature. Then the solvent is removed by evaporation hours at reflux temperature. Then the solvent is removed by evaporation in vacuo. The residue is refluxed during 18 hours with a mixture of 160 ml of 4 N hydrochloric acid, 160 ml of water and 80 ml of acetic acid. The resulting clear solution is made alkaline with aqueous ammonia and the oil which separates is taken up in chloroform contaning some butanol. The organic solution is dried over magnesium sulphate and concentrated. Stirring the residue with methanol causes the product to crystallize. Yield 59%. Melting point 170° – 174° C.

EXAMPLE 70

9,9-Dimethyl-5-ethyl-2'-hydroxy-6,7-benzomorphan

At 75° C and a hydrogen pressure of 30 atmospheres, 2-benzyl-5-ethyl2'-hydroxy-9,9-dimethyl-6,7-benzomorphan hydrobromide (1 g dissolved in 75 ml of methanol) is submitted to catalytic hydrogenolysis with 1 g of 5% palladium on barium sulphate as the catalyst.

Hydrogen uptake stops after 2 hours. The catalyst is removed by filtration and the solvent evaporated in vacuo. The residue is dissolved in water and the solution made alkaline with an excess of ammonia. The above product separates as a crystalline precipitate and is identical with the compound obtained according to example 70. Yield 74%.

EXAMPLE 71

5,9,9-Trimethyl-6,7-benzomorphan

A solution of 16 g of 2,5,9,9-tetramethyl-6,7-benzomorphan in 75 ml of dry chloroform is treated with cyanogen bromide (11.5 g, dissolved in 75 ml of dry chloroform) as described in example 69. Further processing is also carried out as described in that example, giving the above-mentioned compound in a yield of 53%. Melting point 134° – 137° C.

EXAMPLE 72

2'-Hydroxy-5,9,9-trimethyl-6,7-benzomorphan

In a manner similar to the method described in example 69, however, starting from 2'-hydroxy-2,5,9,9-tetramethyl-6,7-benzomorphan, the above-mentioned compound is obtained. Yield 42%. Melting point 110° – 120° C.

EXAMPLE 73

9,9-Dimethyl-5-ethyl-2'-hydroxy-2-(3-methyl-2-butenyl)-6,7-benzomorphan hydrobromide A mixture of 400 mg of 9,9-dimethyl-5-ethyl-2'-hydroxy-6,7-benzomorphan, 300 mg of 3-methyl-2-butenyl-bromide, 250 mg of sodium bicarbonate and 10 ml of dimethylformamide is stirred and heated at 120° C for 3.5 hours. Then the mixture is concentrated in vacuo, ether is added, insoluble material is removed by filtration and the filtrate is evaporated in vacuo. The basic residue is converted to the above-mentioned hydrobromide, which, after recrystallization from ethanol/ether melts at 213° – 215° C. Yield 50%.

EXAMPLE 74

2-Allyl-5-ethyl-2'-hydroxy-9,9-dimethyl-6,7-benzomorphan hydrobromide

In a manner similar to the one described in example 73, however, applying allylbromide, the above-mentioned compound is obtained. Yield 55%. Melting point 207° – 212° C, with decomposition.

EXAMPLE 75

2-Allyl-2'-hydroxy-5,9,9-trimethyl-6,7-benzomorphan hydrobromide

In a manner similar to the method described in example 73, however, starting from 2'-hydroxy-5,9,9-trimethyl-6,7-benzomorphan and applying allylbromide, the above-mentioned compound is obtained. Yield 66%. Melting point, after recrystallization from ethanol/ether, 220° – 225° C, with decomposition.

EXAMPLE 76

2-Cyclopropylmethyl-9,9-dimethyl-5-ethyl-2'-hydroxy-6,7-benzomorphan hydrobromide In a manner similar to the method described in example 73, however, applying cyclopropylmethylbromide, the above-mentioned compound is obtained. Yield 65%. Melting point, after recrystallization from ethanol, 280° – 283° C, with decomposition.

EXAMPLE 77

2-Cyclopropylmethyl-9,9-dimethyl-5-ethyl-2'-hydroxy-6,7-benzomorphan hydrobromide This compound, which has been mentioned in the preceding example already, may also be prepared via the corresponding cyclopropanecarbonyl compound by means of reduction with lithium aluminium hydride. This procedure precludes the formation of the isomeric N-cyclobutyl derivative, a by-product that may arise when using the method described in example 76.

To a solution of 1 g of 9,9-dimethyl-5-ethyl-2'-hydroxy-6,7-benzomorphan in 15 ml of dry pyridine there is added dropwise, with stirring and cooling with ice, 1.4 ml of cyclopropanecarbonylchloride. The solution is stirred for 16 hours at room temperature and then for 1 hour at 60° C. The solution is concentrated by evaporation in vacuo, leaving a residue which is dissolved in ether.

The ethereal solution is washed with 2 N hydrochloric acid and with a saturated aqueous solution of sodium bicarbonate and, after being dried, concentrated in vacuo. The residue consists of the O,N-di(cyclopropylcarbonyl) derivative. A solution of this product in 10 ml of dry tetrahydrofurane is added dropwise to 1.5 g of lithium aluminium hydride suspended in 20 ml of dry tetrahydrofurane, the mixture being stirred and cooled with ice. Stirring is continued at reflux temperature, when, after cooling, 50 ml of wet ether and subsequently 10 ml of water are added carefully. The suspension obtained is filtered and the filtrate, after drying over sodium sulphate is evaporated in vacuo. To a solution of the residue in 10 ml of isopropanol, hydrogen bromide dissolved in acetic acid is added until the mixture is weakly acid (pH 3).

On the addition of 20 ml of ether the above-mentioned product separates in a crystalline form. Yield 77%. Melting point 280° C, with decomposition. There is no difference in gaschromatographic behaviour between this product and the compound obtained according to example 76.

EXAMPLE 78

2-Cyclopropylmethyl-5,9,9-trimethyl-6,7-benzomorphan hydrochloride

In a manner similar to the method described in example 76, however, starting from 5,9,9-trimethyl-6,7-benzomorphan, the above-mentioned compound is obtained. Yield 59%. Melting point 222° – 227° C, with decomposition.

EXAMPLE 79

2-Cyclopropylmethyl-2'-hydroxy-5,9,9-trimethyl-6,7-benzomorphan hydrobromide

The cyclopropylmethyl derivative obtained according to example 78 is nitrated according to the method described in example 69. Yield 50%. Melting point 85° – 93° C. Catalytic reduction, followed by diazotation and treatment with hot diluted sulphuric acid in a way similar to the one described in said example, leads to the above-mentioned compound which is isolated as the hydrobromide. After recrystallization from methanol, the melting point is 268° – 270° C, with decomposition. Yield 53%.

EXAMPLE 80

9,9-Dimethyl-5-ethyl-2'-hydroxy-2-phenethyl-6,7-benzomorphan hydrobromide

To a stirred mixture of 490 mg of 9,9-dimethyl-5-ethyl-2'-hydroxy6,7-benzomorphan, 8 ml of dimethylformamide and 830 mg of potassium carbonate, there is added at room temperature 780 mg of phenacetylchloride within 20 minutes. The mixture is heated during 3 hours at 120° C, cooled, diluted with water and shaken with a mixture of butanol and benzene (2 : 1). The combined extracts are washed with dilute hydrochloric acid and aqueous sodium bicarbonate successively, dried and evaporated.

The residue, consisting of the O,N-di(phenylacetyl) derivative of the starting material, is dissolved in 10 ml of dry tetrahydrofurane whereupon a suspension of 0.5 g of lithium aluminium hydride in 10 ml of dry ether is added to the stirred mixture, at room temperature and in the course of 45 minutes. Stirring is continued at reflux temperature for two hours, whereupon the mixture is cooled with ice and the organo metal complexes are decomposed by the addition of 5 ml of water, followed by 5 ml of 48% hydrobromic acid. The organic solvents are removed by evaporation in vacuo leaving an aqueous solution from which a semi-solid separates. This is gathered by filtration and dissolved in a small volume of ethanol. From this solution the above substance separates as crystals containing one mole of ethanol. This can be removed by heating at 15 mm and 120° C. Yield 29%. The substance melts partly at 140° – 150° C, then resolidifies and finally melts at 222° – 225°C, with decomposition.

EXAMPLE 81

2-Benzyl-9,9-dimethyl-5-ethyl-2'-hydroxy-6,7-benzomorphan hydrobromide

A mixture of 1.8 g of 9,9-dimethyl-5-ethyl-2'-hydroxy-6,7-benzomorphan hydrobromide, 1.7 ml of benzyl chloride, 3 g of potassium carbonate, 2.5 g of potassium iodide and 30 ml of dimethylformamide is stirred and heated to 90° C for 16 hours. The reaction mixture is processed as usually giving a product which may be contaminated with O,N-di-benzylated material. For purification the product is heated with 48% hydrobromic acid at 90° C during 30 minutes. After cooling a solid separates which is gathered and then treated with benzene and aqueous ammonia. The benzene is evaporated and the remaining substance dissolved in a small volume of methanol.

The solution is acidified with hydrogen bromide (dissolved in acetic acid), whereupon methyl ethyl ketone is added and the above compound crystallizes Yield 51%. Melting point 234° – 236° C, with decomposition (after recrystallization from methyl ethyl ketone/methanol).

EXAMPLE 82

2-Benzyl-9,9-dimethyl-5-ethyl-2'-hydroxy-6,7-benzomorphan hydrobromide

In a manner similar to the method described in example 58, however, starting from 1-benzyl-3,3-dimethyl-4-ethyl-2-(p-methoxybenzyl)-4-piperidinol hydrochloride, prepared according to example 57, the abovementioned substance is obtained. The compound may be purified via the O - acetyl derivative (cf. example 66). Melting point 232° – 235° C, with decomposition. The compound is identical with the product obtained according to example 81.

EXAMPLE 83

(+) and (−)
2'-Hydroxy-5,9,9-trimethyl-6,7-benzomorphan

The racemic compound (13.9 g, obtained according to example 72 is dissolved in 1 l of a hot aqueous solution of 20 g of ammonium d(+)-3-bromocamphor-8-sulphonate and 15 ml of 4 N hydrochloric acid. From the solution, on storing in a refrigerator during 16 hours, a slat separates which after recrystallization from water has $\alpha_D + 0.20°$ (2% in ethanol). Yield 4 g.

The mother liquor is concentrated to a volume of 250 ml. After standing at 40° C for 1 hour, the oil which has separated, becomes crystalline. This salt is recrystalized from 200 ml of hot water, giving 7.2 g of a substance with $\alpha_D + 2.00°$ (2% in ethanol).

Additional lots of both salts can be obtained from the mother liquors. Each of the diastereomeric salts is decomposed by shaking with chloroform and 20% aqueous ammonia. From the chloroform extracts the enantiomers can be secured by evaporation of the solvent.

The bases are recrystallized from methanol/acetone (1 : 3). From 3.75 g of the salt with $\alpha_D + 0.20°$ there is obtained 0.75 g of (−) base having $\alpha_D − 2.05°$ (2% in ethanol). The other salt (8.5 g) gives 1.7 g of the (+) base with $\alpha_D + 2.10°$.

EXAMPLE 84

(+) and (−)
9,9-Dimethyl-5-ethyl-2′-hydroxy-6,7-benzomorphan

A hot aqueous solution of 1 l of 17.5 g of ammonium d(+)-3-bromocamphor-8-sulphonate, 13 ml of 4 N hydrochloric acid and 13 g of the racemic compound prepared according to example 69, is allowed to cool to room temperature. After 3 hours the crystals which have separated are collected. Yield 16.3 g, $\alpha_D + 1.50°$ (2% in ethanol). This crude (++) salt is recrystallized from 1 l of water. The solution is cooled in the refrigerator during 16 hours giving coarse crystals of pure (++) salt. Yield 7.2 g, $\alpha_D + 1.80°$. After concentrating the mother liquor to 350 ml, a second crop of 3.8 g of a less pure product can be obtained, $\alpha_D + 1.65°$.

There are no indications that a diastereomeric salt can be isolated from the mother liquors. Therefore, they are combined and made strongly alkaline by means of aqueous ammonia. An oil separates which crystallizes slowly. From this base (8.5 g) 7 g is converted into the 1(−)-3-bromocamphor-8-sulphonate in the same way as described above, i.e. using 9.5 g of ammonium 1(−)-3-bromocamphor-8-sulphonate, 7.1 ml of 4 N hydrochloric acid and 500 ml of hot water. At room temperature a salt separates which is purified by consecutive recrystallization from water and isopropanol giving 6 g of pure (−−) salt, $\alpha_D - 1.83°$. Both enantiomers are secured from their proper salts in the manner described in example 83. Yield 2.1 g with $\alpha_D + 1.50°$ (2% in ethanol) from 6.5 g of the (++) salt, and 1.4 g with $\alpha_D - 1.50°$ (2% in ethanol) from 5 g of the (−−) salt. Both enantiomers appear in two modifications which are interconvertable, viz. one crystallizing from methanol in voluminous needles, the other in coarse crystals (also from methanol). Melting point 190° – 195° C. The melt is turbid but clarifies at 215° C.

EXAMPLE 85

(−)
2-Allyl-9,9-dimethyl-5-ethyl-2′-hydroxy-6,7-benzomorphan hydrobromide

In a manner similar to the method described in example 74, however, starting from (−) 9,9-dimethyl-5-ethyl-2′-hydroxy-6,7-benzomorphan, the above-mentioned enantiomer is obtained. Yield 60%. Melting point, after recrystallization from ethanol/ether, 230° – 240° C with decomposition. $[\alpha]_D^{21} - 106°$ (0.9% in water)[1].

[1] Specific rotations given in this and the following examples may suffer from errors of ±5°.

EXAMPLE 86

(+)
2-allyl-9,9-dimethyl-5-ethyl-2′-hydroxy-6,7-benzomorphan hydrobromide

In a manner similar to the method described in example 85, however, starting from the dextrorotatory enantiomer of 9,9-dimethyl-5-ethyl-2′-hydroxy-6,7-benzomorphan, the above-mentioned compound is obtained. Yield 47%. Melting point, after recrystallization from ethanol/ether, 230° – 240° C, with decomposition. $[\alpha]_D^{21} + 109°$ (0.8% in water).

EXAMPLE 87

(+)
2-Cyclopropylmethyl-9,9-dimethyl-5-ethyl-2′-hydroxy-6,7-benzomorphan hydrobromide In a manner similar to the method described in example 76, however, starting from the dextrorotatory enantiomer of 9,9-dimethyl-5-ethyl-2′-hydroxy-6,7-benzomorphan, the above-mentioned compound is obtained. Yield 32%. Melting point, after recrystallization from ethanol, 295° – 297° C, with decomposition. $[\alpha]_D^{20} + 141°$ (0.7% in dimethylformamide).

In this case, according to gaschromatography, the product appears to be contaminated with 20% of an impurity, probably the isomeric cyclobutyl derivative.

EXAMPLE 88

(−)
2-Cyclopropylmethyl-9,9-dimethyl-5-ethyl-2′-hydroxy-6,7-benzomorphan hydrobromide In a manner similar to the one described in example 77, however, starting from (−) 9,9-dimethyl-5-ethyl-2′-hydroxy-6,7-benzomorphan, the above-mentioned compound is obtained. Yield 72%. Melting point 283° – 285° C, with decomposition. $[\alpha]_D^{20} - 121°$ (1% in dimethylformamide).

EXAMPLE 89

(+)
2-Cyclobutylmethyl-9,9-dimethyl-5-ethyl-2′-hydroxy-6,7-benzomorphan hydrobromide To a solution of 490 mg of (+) 9,9-dimethyl-5-ethyl-2′-hydroxy-6,7-benzomorphan in 7 ml of dry pyridine, there is added dropwise, with stirring and at room temperature, 700 mg of cyclobutane carbonylchloride. Stirring is continued for 3 hours at room temperature and finally 10 minutes at 40° C. The clear, tan reaction mixture is evaporated in vacuo whereupon the residue is shaken with ether and water. The ethereal solution is washed with dilute hydrochloric acid and water, dried and evaporated. A solution of the residue in 25 ml of dry tetrahydrofurane is dropped to a stirred and cooled suspension of 750 mg of lithium aluminium hydride in 15 ml of the same solvent. The mixture is refluxed for 3 hours and subsequently processed as usual. The product is obtained as the hydrobromide which, after recrystallization from ethanol/ether, melts at 285° C, with decomposition. Yield 60%. $[\alpha]_D^{20} + 131°$ (1.2% in dimethylformamide).

EXAMPLE 90

(−)
2-Cyclobutylmethyl-9,9-dimethyl-5-ethyl-2′-hydroxy-6,7-benzomorphan hydrobromide This compound is prepared in a manner similar to the one described in the preceding example for the preparation of the dextrorotatory enantiomer. Melting point 288° C, with decomposition. Yield 60%. $[\alpha]_D^{20} - 126°$ (1.2% in dimethylformamide).

EXAMPLE 91

(+)
2′-Hydroxy-2-(3-methyl-2-butenyl)-5,9,9-trimethyl-6,7-benzomorphan hydrobromide From 235 mg of (+) 2′-hydroxy-5,9,9-trimethyl-6,7-benzomorphan, by reaction with 250 mg of 3-methyl-2- butenylbromide and 300 mg of sodium bicarbonate in 50 ml of methyl ethyl ketone (with stirring at room temperature) the above-mentioned compound is prepared. Yield 40%. Melting point, after recrystallization from isopropanol, 180° – 184° C, with decomposition. $[\alpha]_D^{20} + 125°$ (1.05% in water).

EXAMPLE 92

(−)

2'-Hydroxy-2-(3-methyl-2-butenyl)-5,9,9-trimethyl-6,7-benzomorphan hydrobromide

In a manner similar to the one described in the preceding example, however, starting from (−) 2'-hydroxy-5,9,9-trimethyl-6,7-benzomorphan, the above-mentioned compound is obtained. Melting point 180°– 184° C, with decomposition. Yield 40%. $[\alpha]_D^{20}$ − 135° (1.1% in water).

EXAMPLE 93

(+)

9,9-Dimethyl-5-ethyl-2'-hydroxy-2-(3-methyl-2-butenyl)-6,7-benzomorphan hydrochloride A mixture of 1 g of the (+)-3-bromocamphor-8-sulphate of (+) 9,9-dimethyl-5-ethyl-2'-hydroxy-6,7-benzomorphan, 1 g of potassium carbonate, 1 g of 3-methyl-2-butenyl bromide and 20 ml of dimethylformamide is stirred and heated at 70° – 80° C during 4 hours. After evaporation of the dimethylformamide at reduced pressure, the residue is shaken with chloroform and water. The organic solution, after evaporation, leaves the above compound which is converted into the hydrochloride. It melts at 217° – 222° C, with decomposition. Yield 61%. $[\alpha]_D^{20} + 150°$ (1.1% in water).

EXAMPLE 94

(−)

9,9-Dimethyl-5-ethyl-2'-hydroxy-2-(3-methyl-2-butenyl)-6,7-benzomorphan hydrochloride In a manner similar to the one described in the preceding example, however, starting from the corresponding (—) salt, the above-mentioned compound is obtained in a 58% yield. Melting point 217° – 222° C, with decomposition. $[\alpha]_D^{20}$ − 149° (1% in water).

EXAMPLE 95

9,9-Dimethyl-5-ethyl-2'-hydroxy-2-(2-methyl-allyl)-6,7-benzomorphan hydrobromide A mixture of 500 mg of 9,9-dimethyl-5-ethyl-2'-hydroxy-6,7-benzomorphan, 500 mg of potassium carbonate, 0.3 ml of 2-methyl-allyl-chloride and 30 ml of dimethylformamide is stirred at 50° C for 16 hours. Then the mixture is diluted with water and extracted with petroleum ether. Evaporation of the extract leaves the above-mentioned compound as a base, which is converted into the hydrobromide. Yield 280 mg. Melting point 228° – 230° C, with decomposition.

EXAMPLE 96

2-(3-Butenyl)-9,9-dimethyl-5-ethyl-2'-hydroxy-6,7-benzomorphan hydrobromide

In a manner similar to the one described in example 95, however, applying 4-bromo-1-butene as the alkylating agent, the above-mentioned compound is obtained as the hydrobromide. Melting point 213° – 215° C, with decomposition. Yield 250 mg.

EXAMPLE 97

2-(2-Chloro-allyl)-9,9-dimethyl-5-ethyl-2'-hydroxy-6,7-benzomorphan hydrochloride A mixture of 500 mg of 9,9-dimethyl-5-ethyl-2'-hydroxy-6,7-benzomorphan, 500 mg of potassium carbonate, 0.3 ml of 2,3-dichloro-1-propene and 30 ml of dimethylformamide is stirred at room temperature for 16 hours, whereupon another 0.2 ml of 2,3-dichloro-1-propene is added and stirring is continued for 4 hours at 40° C. Then the mixture is diluted with water and extracted with petroleum ether. Evaporation of the extract gives a residue which is heated with 1N hydrochloric acid for 2 hours, in order to hydrolyse some O-alkylation product. After basification with an excess of aqueous ammonia and extraction with benzene, the above-mentioned compound is obtained by evaporation of the extract. Conversion into the hydrochloride gives a product melting at 230° – 232° C, with decomposition. Yield 100 mg.

EXAMPLE 98

9,9-Dimethyl-5-ethyl-2'-hydroxy-2-propargyl-6,7-benzomorphan hydrochloride

In a manner similar to the one described in example 97, however, using propargyl chloride as the alkylating agent, the above-mentioned compound is obtained. Melting point 218°– 220° C, with decomposition. Yield 180 mg.

EXAMPLE 99

2-(2-Cyclohexen-1-yl)-9,9-dimethyl-5-ethyl-2'-hydroxy-6,7-benzomorphan

By reaction of 245 mg of 9,9-dimethyl-5-ethyl-2'-hydroxy-6,7-benzomorphan with 200 mg of 3-bromo-cyclohexene and 200 mg of potassium carbonate in 500 ml of methyl ethyl ketone, the above-mentioned compound is obtained. Yield 61%. Melting point 122° – 125° C, after recrystallization from petroleum ether.

EXAMPLE 100

2-(2-Cyclohexyliden-ethyl)-9,9-dimethyl-5-ethyl-2'-hydroxy-6,7-benzomorphan hydrobromide In a manner similar to the one described in example 99, however, applying (2-bromo-ethylidene)-cyclohexane, the above-mentioned compound is obtained. Yield 50%. Melting point 205°– 208° C, with decomposition.

EXAMPLE 101

2-(1-Cyclohexen-1-yl-methyl)-9,9-dimethyl-5-ethyl-2'-hydroxy-6,7-benzomorphan hydrochloride In a manner similar to the method described in example 99, however, applying 1-chloromethylcyclohexene, the above compound is obtained. Yield 45%. Melting point 230° – 233° C, with decomposition.

EXAMPLE 102

2'-Acetoxy-5-ethyl-2,9,9-trimethyl-6,7-benzomorphan oxalate

The acetylation of 5-ethyl-2'-hydroxy-2,9,9-trimethyl-6,7-benzomorphan is carried out as described in example 69. As the crude product fails to crystallize it is converted into the acid oxalate. Yield 48%. Melting point 180° – 185° C, with decomposition.

EXAMPLE 103

5-Ethyl-2'-propionyloxy-2,9,9-trimethyl-6,7-benzomorphan oxalate

In a manner similar to the one described in the preceding example, the above-mentioned compound is obtained as the acid oxalate. Yield 46%. Melting point 168° – 170° C, with decomposition.

EXAMPLE 104

5-Ethyl-2'-nicotinoyloxy-2,9,9-trimethyl-6,7-benzomorphan oxalate

This compound is prepared by reaction of 518 mg of 5-ethyl-2'-hydroxy-2,9,9-trimethyl-6,7-benzomorphan with 425 mg of nicotinoyl chloride in 20 ml of dry pyridine during 16 hours at room temperature. After evaporation of the solvent in vacuo, the residue is shaken with petroleum ether and aqueous ammonia. The petroleum ether solution is fractionated by chromatography on aluminium oxide. The product is secured as the acid oxalate, which crystallizes with 2 moles of water. Yield 55%. Melting point 202° – 204° C, with decomposition.

EXAMPLE 105

5-Ethyl-2'-methoxymethoxy-2,9,9-trimethyl-6,7-benzomorphan oxalate

A mixture of 2 g of 5-ethyl-2'-hydroxy-2,9,9-trimethyl-6,7-benzomorphan, 20 ml of 1,2-dimethoxyethane and 240 mg of sodium hydride (as a 50% suspension in oil) is heated at 80° C for 2 hours. The clear solution is cooled with ice and 8.8 g of chloromethyl methyl ether is added. After standing at room temperature during 16 hours, the mixture is processed as described in example 104, giving the above compound as the acid oxalate, crystallizing with 2 moles of water. Melting point 158° – 160° C, with decomposition. Yield 41%.

EXAMPLE 106

5-Ethyl-2'-methoxy-2,9,9-trimethyl-6,7-benzomorphan oxalate

To a stirred solution of 1 g of 5-ethyl-2'-hydroxy-2,9,9-trimethyl-6,7-benzomorphan and 2 g of potassium hydroxyde in 50 ml of methanol and 3 ml of water, there is added, at room temperature and within 2 hours, a solution of 2.15 g of N-nitroso-N-methyl-p-toluene-sulphonamide in 20 ml of ether. After continued stirring (1 hour), another quantity of 2.15 g of the nitroso amide is added in the same way.

After 16 hours the suspension is filtered, whereupon the filtrate is acidified to pH 3 with 4N sulphuric acid in order to decompose the excess of diazomethane. After concentration of the mixture in vacuo it is shaken with petroleum ether and aqueous ammonia. Evaporation of the solvent leaves the substance as a base which is converted into the acid oxalate containing 2 moles of water of crystallization. Melting point 158° – 160° C, with decomposition.

EXAMPLE 107

2'-Benzoyloxy-5-ethyl-2,9,9-trimethyl-6,7-benzomorphan oxalate

In a manner similar to the method described in example 105, however, applying benzoyl chloride instead of chloromethyl methyl ether, the above-mentioned compound is obtained as the acid oxalate. Melting point 223° – 225° C, with decomposition. Yield 73%.

EXAMPLE 108

(−)
2-(3-Bromo-3-methyl-butyl)-9,9-dimethyl-5-ethyl-2'-hydroxy-6,7-benzomorphan hydrobromide A mixture of 250 mg of (−)-9,9-dimethyl-5-ethyl-2'-hydroxy-6,7-benzomorphan, 30 ml of methanol, 300 mg of N-ethyl diisopropylamine and 0.3 ml of 3-methyl-2-butenylbromide is stirred at room temperature for 16 hours. After removal of the solvent by evaporation, the residue is shaken with chloroform and ammonia. The chloroform solution is evaporated to leave a base which is dissolved in a small quantity of isopropanol and then treated at 90° C with concentrated hydrobromic acid. The mixture is evaporated to dryness and the solid thus obtained is recrystallized from isopropanol/acetone. The above compound melts at 185° – 190° C, with decomposition. Yield 170 mg. $[\alpha]_D^{20}$ − 82° (1% in methanol).

Tests were conducted with respect to the pharmacological properties of various 6,7-benzomorphans according to this invention which are included within general formula II above, and in which the substituents R, $R_1$, $R_2$ and $R_3$ are as indicated in the below Table A. The tests conducted were as follows:

(1) Tail Withdrawal Test In Rats

The analgesic potency of the tested compounds was determined by the so-called tail withdrawal test in male rats having a body weight of 250 ± 10 g. substantially in accordance with the standard procedures described by Janssen P. A. J., Niemegeers C. J. E. and Dony J. G. H.; Arzneim Forsch, 13, 502 (1963). The test procedures were substantially as described, with the exceptions that measurements were made more frequently, the cut-off time was reduced from 15 seconds to 10 seconds, and the results were rated according to three different levels of analgesia, defined as follows:

(a) Moderate analgesia (M.A. on Table A) - the tail withdrawal reaction time is >6 and <10 seconds.

(b) Pronounced analgesia (P.A. on Table A) - no tail withdrawal response over a reaction time >10 seconds, but slight movements of the tail in the warm water cup.

(c) Surgical analgesia (S.A. on Table A) - no tail withdrawal response over a reaction time >10 seconds, and no movements or reaction of the tail.

Table A gives the dosages, in mg./kg of body weight, administered subcutaneously that constitute the $ED_{50}$-values and confidence limits for each of the defined compounds to achieve the above defined levels of analgesia (M.A., P.A. and S.A.). For purposes of comparison, Table A also gives the corresponding values for Nalorphine and Pentazocine.

(2) Nalorphine-like Activity In Rats

In order to test the Nalorphine-like activity of the tested compounds, that is, the potency of such compounds in reversing the respiratory depression, loss of righting reflex, muscular rigidity, surgical analgesia and blockage of the corneal and pinna reflexes resulting from the administration of high doses of fentanyl, male Wistar rats were given a subcutaneous injection of 0.63 mg/kg body weight of fentanyl to induce the described phenomena. 30 minutes after the fentanyl dose, the same animals received intravenous injections of the identified test compounds and of Nalorphine and Pentazocine for comparison purposes. Table A indicates the lowest active dose, in mg/kg body weight, exhibiting nalorphine-like properties, that is, capable of immediately reversing the mentioned phenomena induced by the dosage of fentanyl.

(3) Writhing Test In Rats

Female Wistar rats were injected with ½ ml. of a 1%-solution of acetic acid I.P. and the number of writhings during the 60 minutes following the injection were noted. In control animals, the mean number of writhings was 100 during the 60 minutes following the injection of acetic acid solution. The various test compounds identified on Table A, and also Nalorphine and Pentazocine for the purposes of comparison, were administered subcutaneously 30 minutes prior to the standard injection of acetic acid. Table A gives, for each test compound, the lowest active dosage, in mg/kg body weight, that reduced the number of writhings by at least one-half, that is <50 writhings in the 60 minutes following the acetic acid injection.

1. A compound selected from the group consisting of substituted 2-benzyl-4-piperidones having the formula

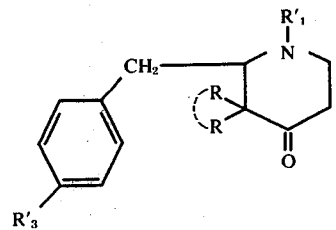

in which the substituents R, when taken separately, are methyl or ethyl, or, when taken together with the carbon atom to which they are bonded, form cyclopentyl or cyclohexyl, $R'_1$ is selected from the class consisting of hydrogen atom, methyl and benzyl, and $R'_3$ is selected from the class consisting of hydrogen atom, hydroxy and methoxy, and halide salts of said substituted 2-benzyl-4-piperidones.

2. A compound according to claim 1, in which each

TABLE A

| $R_1$ | $R_2$ | $R_3$ | R | R | base salt | Tail withdrawal test M.A. | P.A. | S.A. | Nalorphine-like activity | Writhing test |
|---|---|---|---|---|---|---|---|---|---|---|
| CH₃ | CH₃ | OH | CH₃ | CH₃ | HCl | 0.40 | 0.50 | 0.63 | — | — |
| CH₃ | C₂H₅ | OH | CH₃ | CH₃ | — | 0.08 | 0.10 | 0.12 | — | — |
| CH₃ | nC₃H₇ | OH | CH₃ | CH₃ | — | 0.12 | 0.16 | 0.20 | — | — |
| CH₃ | C₆H₅ | OH | CH₃ | CH₃ | — | 0.08 | 0.16 | 0.31 | — | — |
| CH₃ | H | H | C₂H₅ | C₂H₅ | HCl | >2.5 | >2.5 | >2.5 | — | — |
| CH₃ | H | H | (CH₂)₅ | | HCl | >10 | >10 | >10 | — | — |
| CH₂—CH=C(CH₃)₂ | C₂H₅ | OH | CH₃ | CH₃ | HBr | 1.25 | 3.5 | 4.0 | — | — |
| CH₂—CH=CH₂ | C₂H₅ | OH | CH₃ | CH₃ | HBr | >2.5 | >2.5 | >2.5 | 0.04 | >0.16 |
| CH₂—CH=CH₂ | CH₃ | OH | CH₃ | CH₃ | HBr | ~2.5 | >2.5 | >2.5 | 0.02 | >0.16 |
| CH₂—C₃H₅ | C₂H₅ | OH | CH₃ | CH₃ | HBr | >2.5 | >2.5 | >2.5 | 0.02 | 0.16 |
| CH₂—C₃H₅ | CH₃ | OH | CH₃ | CH₃ | HBr | 1.25 | 2.5 | >2.5 | 0.02 | >0.16 |
| CH₂—CH₂—C₆H₅ | C₂H₅ | OH | CH₃ | CH₃ | HBr | 0.25 | 0.25 | 0.50 | — | — |
| CH₂—C₆H₅ | C₂H₅ | OH | CH₃ | CH₃ | HBr | >10 | >10 | >10 | >2.5 | — |
| CH₂—CH=CH₂ | C₂H₅ | OH | CH₃ | CH₃ | (−) HBr | >2.5 | >2.5 | >2.5 | 0.01 | >0.16 |
| CH₂—CH=CH₂ | C₂H₅ | OH | CH₃ | CH₃ | (+) HBr | >2.5 | >2.5 | >2.5 | >0.16 | — |
| CH₂—C₃H₅ | C₂H₅ | OH | CH₃ | CH₃ | (+) HBr | >2.5 | >2.5 | >2.5 | >0.16 | — |
| CH₂—C₃H₅ | C₂H₅ | OH | CH₃ | CH₃ | (−) HBr | >2.5 | >2.5 | >2.5 | 0.01 | >0.16 |
| CH₂—C₃H₇ | C₂H₅ | OH | CH₃ | CH₃ | (+) HBr | ~2.5 | >2.5 | >2.5 | >0.16 | — |
| CH₂—C₃H₇ | C₂H₅ | OH | CH₃ | CH₃ | (−) HBr | 0.31 | ~2.5 | >2.5 | 0.04 | 0.08 |
| CH₂—CH=C(CH₃)₂ | CH₃ | OH | CH₃ | CH₃ | (+) HBr | >2.5 | >2.5 | >2.5 | >0.16 | — |
| CH₂—CH=C(CH₃)₂ | CH₃ | OH | CH₃ | CH₃ | (−) HBr | ~2.5 | >2.5 | >2.5 | >0.16 | 0.63 |
| CH₂—CH=C(CH₃)₂ | C₂H₅ | OH | CH₃ | CH₃ | (+) HCl | >10 | >10 | >10 | >0.16 | — |
| CH₂—CH=C(CH₃)₂ | C₂H₅ | OH | CH₃ | CH₃ | (−) HCl | 0.31 | 0.31 | 2.5 | >0.16 | 0.31 |
| CH₂—C.CH₃=CH₂ | C₂H₅ | OH | CH₃ | CH₃ | HBr | >10 | >10 | >10 | >0.16 | — |
| CH₂—CH₂—CH=CH₂ | C₂H₅ | OH | CH₃ | CH₃ | HBr | 0.16 | 0.31 | 5.0 | >0.16 | — |
| CH₂—C.Cl=CH₂ | C₂H₅ | OH | CH₃ | CH₃ | HCl | >10 | >10 | >10 | >0.16 | — |
| CH₂—C≡CH | C₂H₅ | OH | CH₃ | CH₃ | HCl | >10 | >10 | >10 | 0.08 | — |
| CH₂—⌬ | C₂H₅ | OH | CH₃ | CH₃ | — | >2.5 | >2.5 | >2.5 | >0.63 | >2.5 |
| CH₂—CH=⌬ | C₂H₅ | OH | CH₃ | CH₃ | HBr | >2.5 | >2.5 | >2.5 | >0.63 | 2.5 |
| CH₂—⌬ | C₂H₅ | OH | CH₃ | CH₃ | HCl | ≧10 | >10 | >10 | >0.16 | >2.5 |
| CH₃ | C₂H₅ | OCOCH₃ | CH₃ | CH₃ | C₂H₂O₄ | 0.02 | 0.04 | 0.08 | >0.16 | — |
| CH₃ | C₂H₅ | OCOC₂H₅ | CH₃ | CH₃ | C₂H₂O₄ | 0.04 | 0.08 | 0.31 | >0.16 | — |
| CH₃ | C₂H₅ | OCOC₅H₃N[r] | CH₃ | CH₃ | C₂H₂O₄ | 0.04 | 0.08 | 0.31 | — | — |
| CH₃ | C₂H₅ | OCH₂OCH₃ | CH₃ | CH₃ | C₂H₂O₄ | 1.25 | 2.5 | 5.0 | — | — |
| CH₃ | C₂H₅ | OCH₃ | CH₃ | CH₃ | C₂H₂O₄ | 0.31 | 1.25 | >2.5 | — | — |
| CH₃ | C₂H₅ | OCOC₆H₅ | CH₃ | CH₃ | C₂H₂O₄ | 0.08 | 0.08 | 0.31 | — | — |
| CH₂—CH₂—C(CH₃)₂Br | C₂H₅ | OH | CH₃ | CH₃ | (−) HBr | 0.31 | 1.25 | 2.5 | >0.16 | 0.31 |
| Nalorphine | | | | | | 20 | >40 | >40 | 0.31 | 0.20 |
| Pentazocine | | | | | | 5.0 | 40 | >160 | 5.0 | 20 |

[r] NC₅H₃CO = nicotinoyl.

of said substituents R is a methyl group.

3. A compound according to claim 1, in which $R'_3$ is selected from the class consisting of hydroxy and methoxy groups.

What is claimed is:

* * * * *